(12) United States Patent
Tarasev et al.

(10) Patent No.: US 11,933,780 B2
(45) Date of Patent: Mar. 19, 2024

(54) SYSTEM AND METHOD FOR ASSESSING AN EFFECT ON CELLULAR UNITS IN AN ORGANISM

(71) Applicant: Functional Fluidics Inc., Detroit, MI (US)

(72) Inventors: Michael Tarasev, Pinckney, MI (US); Xiufeng Gao, Windsor (CA); Marta Ferranti, Chesterfield, MI (US)

(73) Assignee: Functional Fluidics Inc., Detroit, MI (US)

( * ) Notice: Subject to any disclaimer, the term of this patent is extended or adjusted under 35 U.S.C. 154(b) by 0 days.

(21) Appl. No.: 17/889,902

(22) Filed: Aug. 17, 2022

(65) Prior Publication Data
US 2024/0060958 A1    Feb. 22, 2024

(51) Int. Cl.
| | | |
|---|---|---|
| *G01N 33/49* | (2006.01) | |
| *C07K 14/805* | (2006.01) | |
| *C12N 5/078* | (2010.01) | |
| *C12N 9/02* | (2006.01) | |
| *C12Q 1/26* | (2006.01) | |

(Continued)

(52) U.S. Cl.
CPC ....... *G01N 33/4925* (2013.01); *C07K 14/805* (2013.01); *C12N 5/0641* (2013.01); *C12N 9/0069* (2013.01); *C12Q 1/26* (2013.01); *G01N 33/5026* (2013.01); *G01N 33/721* (2013.01); *G01N 33/80* (2013.01); *G01N 2333/90241* (2013.01)

(58) Field of Classification Search
CPC .......... G01N 33/4925; G01N 33/5026; G01N 33/721; G01N 33/80; G01N 2333/90241; C07K 14/805; C12N 5/0641; C12N 9/0069; C12Q 1/26
See application file for complete search history.

(56) References Cited

U.S. PATENT DOCUMENTS

2022/0074955 A1    3/2022 Tarasev et al.

OTHER PUBLICATIONS

Tarasev et al., "Individual variability in response to a single sickling event for normal, sickle cell, and sickle trait erythrocytes", 2017, Elsevier, Translation Research, vol. 181, 96-107. (Year: 2017).*

(Continued)

*Primary Examiner* — Jennifer Wecker
*Assistant Examiner* — Kathryn Elizabeth Limbaugh
(74) *Attorney, Agent, or Firm* — Reising Ethington P.C.

(57) ABSTRACT

A method for assessing an effect, such as a treatment, disease, or passage of time on a cellular unit of an organism includes providing a sample including a cellular unit subject to the effect in a supporting medium in a hermetically sealed container. The container is deoxygenated to induce at least one of a predetermined amount of hypoxia and a predetermined rate of oxygen consumption in the medium. Values for variables associated with the medium and/or the cellular unit are determined at each of a plurality of different times. Various combinations of the predetermined amount of hypoxia, the predetermined rate of oxygen consumption, the values for the variables associated with the medium and/or cellular unit, and the times and then correlated to generate a multi-dimensional surface. This surface is compared with another surface correlating corresponding values relating to another cellular unit such as one not subject to the effect.

20 Claims, 10 Drawing Sheets

(51) Int. Cl.
   *G01N 33/50*   (2006.01)
   *G01N 33/72*   (2006.01)
   *G01N 33/80*   (2006.01)

(56) References Cited

OTHER PUBLICATIONS

Atiken, C. E. et al. "An Oxygen Scavenging System for Improvement of Dye Stability in Single-Molecule Fluorescence Experiments" 94, Biophysical Journal, pp. 1826-1835 (Mar. 2008).

Henry, E.R. et al., "Allosteric control of hemoglobin S fiber formation by oxygen and its relation to the pathophysiology of sickle cell disease" Proc. 117 Natl. Acad. Sci. U.S.A. No. 26 pp. 15018-15027 (Jun. 2020).

Patil, P. V. et al. "The Use of Protocatechuate Dioxygenase for Maintaining Anaerobic Conditions in Biochemical Experiments" 286 Analytical Biochemistry pp. 187-192 (Nov. 2000).

Rotman, H.H. et al. "Kinetics of Oxygenation and Deoxygenation of Erythrocytes Containing Hemoglobin S," 21 Respiration Physiology 1 pp. 9-17 (Jul. 1974).

Vandergriff, Kim D. et al. "Hemoglobin-Oxygen Equilibrium Curves Measured During Eznymatic Oxygen Consumption," 256 Analytical Biochemistry No. 1 pp. 107-116 (Feb. 1998).

Weigand, Mitchell R. H. et al. "Magnetophoretic and Spectral Characterization of Oxyhemoglobin and Deoxyhemoglobin: Chemical Versus Enzymatic Processes" PLoS One (Journal of Public Library of Science) (Sep. 2021).

\* cited by examiner

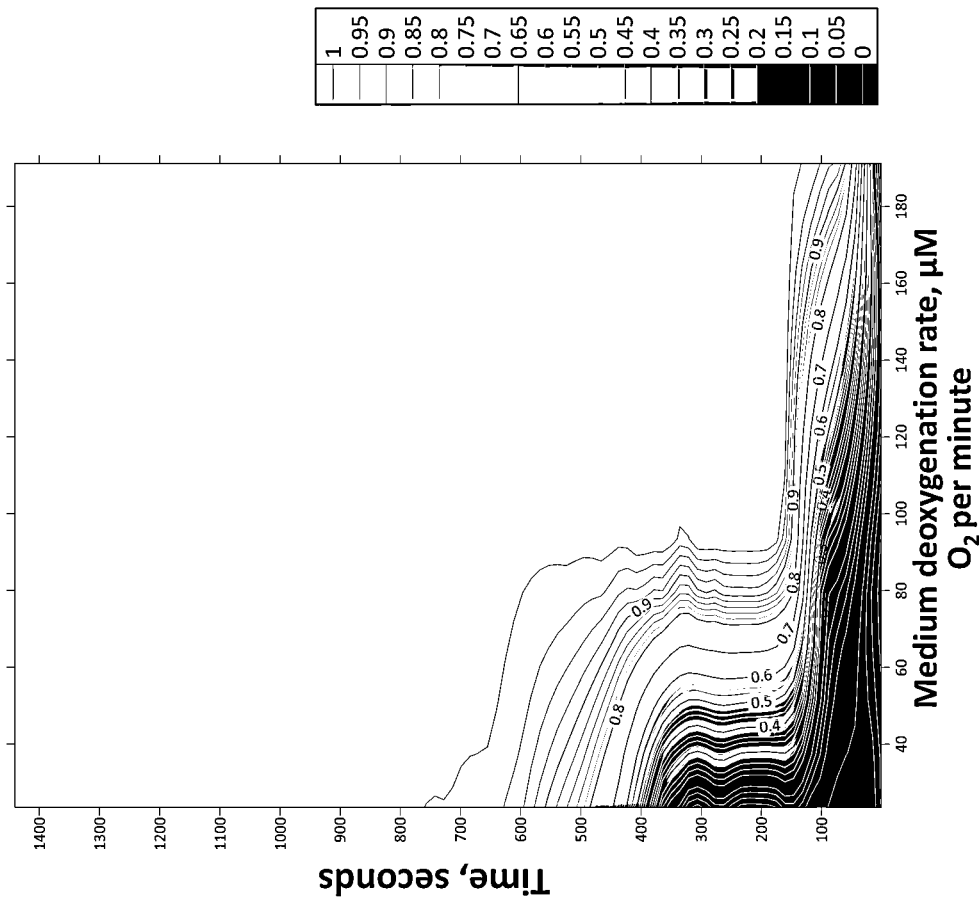
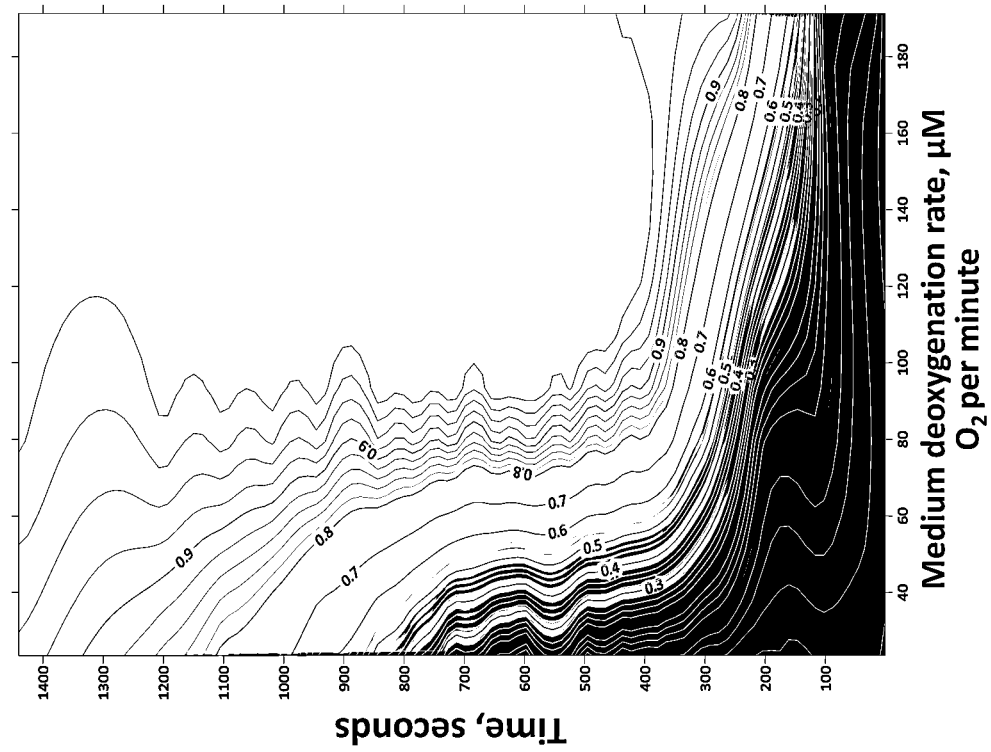

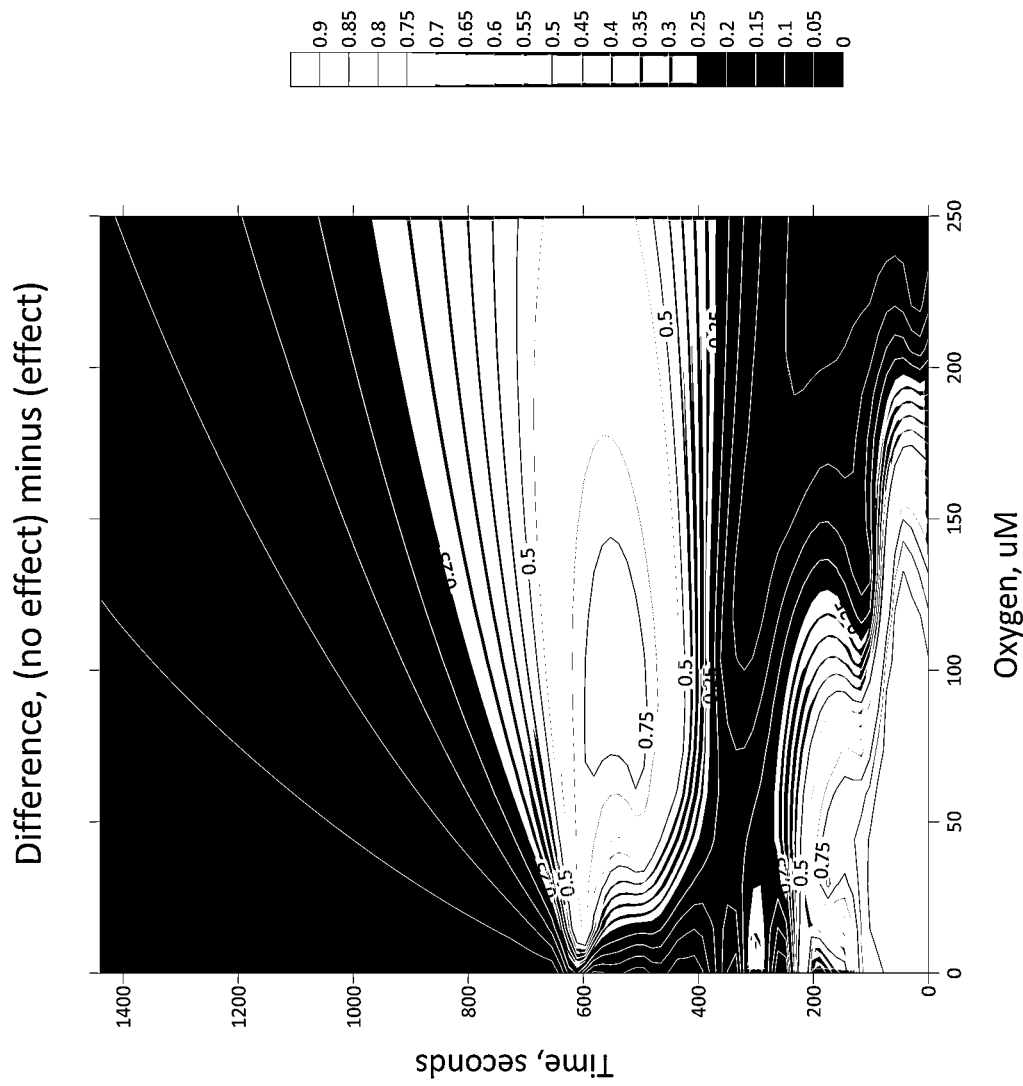

SYSTEM AND METHOD FOR ASSESSING AN EFFECT ON CELLULAR UNITS IN AN ORGANISM

BACKGROUND OF THE INVENTION a. Field of the Invention

This disclosure relates to a system and method for assessing an effect, such as a disease, treatment, or passage of time on a cellular unit of an organism. In particular, this disclosure relates to a system and method that is capable of assessing effects on cellular units at varying levels of hypoxia and rates of oxygen consumption and under both equilibrium and non-equilibrium conditions.

b. Background Art

Hypoxia in medicine is a condition where tissues or organs experience depleted oxygen supply. It can be either systemic, in that it would affect the whole organism, or localized, in that it would affect only a particular tissue, organ or body part. Conditions under normal atmospheric oxygen pressure are typically referred to as "normoxia", and conditions with extremely low or no oxygen are referred to as "severe hypoxia", or "anoxia". As used herein, "hypoxia" refers to any condition with less than a normoxic amount of oxygen present while an "amount of hypoxia" or "level of hypoxia" refers to a decreased oxygen concentration or partial pressure of oxygen ($PO_2$) below normoxic, with "increased" hypoxia referring to lower $PO_2$ and "severe hypoxia" referring to conditions with less that 5% of normoxic $PO_2$.

Hypoxia is an integral part of the normal cell physiology. Each organ and tissue is characterized by its own unique partial oxygen pressure ($PO_2$) arising form the balance between oxygen delivery and consumption. In blood, hypoxic conditions arise during oxygen delivery, reflected in oxygen saturation changes between arterial and venous blood. Tissue hypoxia can be elevated when compensatory mechanisms are not able to support the demand for oxygen—for example during strenuous exercise. Tissue hypoxia can also be affected by external conditions such as low atmospheric oxygen at high altitude. Tissue hypoxia may also change as a result of pathology, due to a desirable or undesirable effect of a drug, or as a result of cell membrane damage and/or modification. Cell membrane damage can be caused, for example, by blood storage, ex-vivo manipulation blood, or in-vivo interaction with implanted medical devices.

One of the tissues that is affected by hypoxia is blood, particularly erythrocytes (Red Blood Cells (RBC)), with hypoxia in this case affecting changes in oxygen load of the blood oxygen carrier, hemoglobin (Hb). Hypoxia in blood (hypoxemia) brings about a re-equilibration between plasma oxygen and the level of hemoglobin oxygenation. Lower external oxygen tension (partial oxygen pressure ($PO_2$)) in blood plasma leads to a lower concentration of the oxygenated form of Hb (Oxy-Hb) and to an increased concentration of the deoxygenated form of Hb (Deoxy-Hb). These values are tightly correlated such that hemoglobin deoxygenation can be estimated from oxygen tension in blood plasma using well-known oxygen dissociation curves illustrating a generally sigmoidal relationship. Increased accuracy can be achieved by further accounting for other physiological factors such as pH or 2,3-Diphosphoglycerate (2,3-DPG) that impact oxygen uptake and delivery and result in shifts in these curves. Clinically, the potential of harmful effects of blood hypoxia are well recognized, as well as the possibility of harm from elevated oxygen content due to excess oxygen administration. Therefore, it is sometimes desirable to investigate the effects of hypoxia on erythrocytes and/or on hemoglobin, whether contained within erythrocytes or free in a solution such as in blood plasma or in an additive storage solution as used for packed RBC storage for blood transfusion.

As mentioned above, tissue hypoxia may change as a result of pathology. For example, Sickle Cell Disease (SCD), a hereditary blood disease, can impact blood hypoxia, especially in organs such as the spleen. SCD is one of most common hereditary blood disorders and affects up to 100,000 people in the United States alone. Up to 2 million people are estimated to carry the sickle cell trait and it has been estimated that the number of people with SCD may increase by about 30% globally by 2050. Treatment of SCD imposes significant burdens on healthcare systems and results in significant lost productivity for patients. SCD is caused by a mutation in the HBB gene responsible for the production of hemoglobin (Hb), resulting in the so-called "sickled" RBC, which contain an abnormal Hb form, called sickle hemoglobin (HbS). Polymerization of deoxygenated HbS in cells with sufficiently high content of HbS results in generation of fibers within the cells that make the cells more rigid, disrupt normal oxygenation-deoxygenation cycle (e.g., by altering the kinetics of deoxygenated Hb interaction with membrane structural elements) and cause reversible or irreversible RBC deformations, including the development of a characteristic sickle-like cell shape, which gave the disease its name.

Over time, sickling of RBC results in a vastly reduced erythrocyte lifespan, down to about 20 days from the normal average of 110-120 days. Additionally, a vast array of SCD-related complications, including life-threatening, are the result of this reduced erythrocyte lifespan. For example, the potential of such hypoxia-induced polymerization to cause plasma membrane damage had been proposed previously. Cycles of Hb-S deoxygenation with associated polymerization and re-oxydation with polymer melting were shown to critically impact membrane structural proteins, like Band-3 complex, resulting in membrane microvesiculation.

Hypoxia is an integral part of SCD pathophysiology, leading to a wide range of SCD-associated complications including vaso-occlusive phenomena. Tissue oxygenation, and thus resultant oxygen tension in patients with SCD may differ from that of non-SCD subjects due to the compromised total oxygen carrying capacity of SCD blood compounded by possible changes in microcirculation (e.g., due to partial or total vessel blockage resulting from elevated cell adhesion to the endothelium in a vessel). That may led to a wider deviations from "steady-state" tissue oxygenation levels at times of elevated oxygen consumption in tissues or organs, when physiological compensatory mechanisms can not fully compensate for decreased oxygen availability, exasperated by, for example, reduced RBC numbers/lower total Hb concentration and the presence of irreversibly deformed RBC. The percentage of sickled cells after deoxygenation is the basis of the standard "sickling assay" (where sickling can be induced by either low oxygen tension or change in pH) and has been used previously as a predictor of disease outcomes. Notably, the amount of sickling will significantly depend on the level of hypoxia, with more severe hypoxia resulting in more sickling, and thus potentially in more membrane damage.

The influence of hypoxia in SCD is not limited to just that arising from HbS polymerization. The interaction of the deoxygenated form (Deoxy) of HbS with cytoplasmic domain band 3 protein (cdb3) is much stronger than that of standard adult hemoglobin HbA, with a portion of Deoxy HbS being irreversibly bound to the complex. Even the reversibly bound fraction of Deoxy HbS has been shown to dissociate much more slowly than Deoxy HbA, impacting sickle RBC membrane properties. Production of superoxide, facilitated under hypoxic conditions and exacerbated in SCD, is a source of potential oxidative damage to RBC membranes. Oxidative damage causes a multitude of defects in membrane structures critically involved in regulation of erythrocyte membrane stability and function. Previously, Reactive Oxygen Species (ROS)-induced damage was linked with irreversible micro-rheologic abnormalities of sickle RBC membranes. Abnormal HbS membrane interactions have also been associated with the decline of nitric oxide (NO) and antioxidant bioavailability, and has been suggested as a key factor in accelerated sickle RBC senescence. It had been suggested that cycles of hypoxia, with consequent chronic and systemic oxidative stress, repeatedly generating great amounts of ROS, could lead to a cyclic cascade characterized by elevated cell adhesion, hemolysis, vaso-occlusion, and ischemia-reperfusion injury. It has been suggested, that these factors may be significant features of SCD phenotype variations.

Treatment of SCD presents significant difficulties. In particular, treatment requires ensuring adequate oxygen supply to organs and tissues while also reducing the risks of RBC sickling and related complications including vaso-occlusive events that can further compromise oxygen delivery and lead to pain crises, acute chest syndrome and stroke, among other conditions. Some of the conditions that are favorable for oxygen delivery (e.g., a relatively high concentration of hemoglobin in red blood cells or a relatively low hemoglobin oxygen affinity) are also favorable for RBC sickling. Conversely, treatments that may reduce RBC sickling (e.g., by modifying hemoglobin or changing the concentration of 2,3 diphosphoglyceric acid in red blood cells) can decrease oxygen delivery.

Because of the significant physiological and financial impacts of SCD, there is a pressing need for assays to both assess patient conditions and to monitor the progress of SCD therapies that affect Hb oxygen affinity and Hb polymerization kinetics. The pathology of SCD, however, creates difficulties for development of such assays.

HbS sickling can be described in terms of how fast it occurs (rate of sickling) and how much hemoglobin is being polymerized (extent of sickling). Both the rate and the extent of sickling, however, depend on a multitude of factors including, for example, HbS concentration, pH, temperature, and level (degree) of hypoxia. Under physiological conditions the rates of oxygen binding and dissociation with hemoglobin are very fast (milliseconds), thus the ratio between oxygenated and deoxygenated Hb forms during, for example, a one second duration of blood flow through microcirculation is determined primarily by changes in the partial oxygen pressure in the environment. Considering the transit times, potentially affected by transient RBC adhesion to endothelium in blood vessels, and different and variable levels of hypoxia possible throughout the circulatory system and in the perfused organs, local levels of hypoxia would be an important factor affecting HbS polymerization.

It has also been shown that for sickle RBC the type of sickled hemoglobin polymerization (resulting in potentially different hypoxic RBC morphology) depends on sickle Hb concentration, and importantly on the rate of development of hypoxemia. For example, it has been shown that gradual hypoxia development and thus gradual Hb deoxygenation favors the development of so-called "sickle" and "holly leaf" RBC morphological shapes, while fast hypoxia development and thus fast Hb deoxygenation favors the development of the so-called "granular" RBC morphological state. Resultant RBC morphology is mainly determined by the total number of the aligned hemoglobin polymers and the configuration of each polymer domain in the cell. It can also depend on the cell membrane rigidity and the HbS polymer growth rate, dependent in turn on the hypoxia development rate and HbS deoxygenation. Overall, the severity of hypoxia and the rate of its development are critical parameters both in the HbS polymerization and polymer melting, with the potential to significantly affect cell membrane properties and oxygen transport.

Despite the importance of hypoxia level and rate of oxygen consumption to HbS polymerization and sickling, conventional assays are typically unable to simulate specific levels of hypoxia and rates of deoxygenation, much less correlate this information with related variables associated with red blood cells or hemoglobin such as a change in morphology of an erythrocyte. Further, conventional assays typically mimic equilibrium conditions. While these assays may be useful for simulating longer term effects of SCD, the assays are unable to simulate in vivo conditions for SCD in which reactions such as (i) decreases in oxygen concentration and hemoglobin deoxygenation, (iii) hemoglobin deoxygenation and hemoglobin polymerization and (iii) hemoglobin polymerization and changes in cell morphology do not proceed in equilibrium.

The inventors herein have recognized a need for a system and method to assess an effect, such as a treatment, disease, or passage of time, on a cellular unit of an organism that will minimize and/or eliminate one or more of the above-identified deficiencies.

BRIEF SUMMARY OF THE INVENTION

This disclosure relates to a system and method for assessing an effect, such as a disease, treatment, or passage of time on a cellular unit of an organism. In particular, this disclosure relates to a system and method that is capable of assessing effects on cellular units at varying levels of hypoxia and rates of oxygen consumption and under both equilibrium and non-equilibrium conditions.

A method for assessing an effect on a cellular unit of an organism in accordance with one embodiment includes providing a first aliquot of a first sample including a first cellular unit not subject to the effect in a first supporting medium in a first hermetically sealed container. The method further includes providing a first aliquot of a second sample including a second cellular unit subject to the effect in a second supporting medium in a second hermetically sealed container. The method further includes deoxygenating the first supporting medium and the second supporting medium to induce at least one of a predetermined amount of hypoxia and a predetermined rate of oxygen consumption in the first supporting medium and in the second supporting medium. The method further includes determining, during deoxygenation of the first supporting medium, values for one or more variables associated with the first supporting medium at each of a first plurality of different times and/or values for one or more variables associated with the first cellular unit at each of the first plurality of different times. The method further includes determining, during deoxygenation of the second supporting medium, values for one or more variables associated with the second supporting medium at each of a second plurality of different times and/or values for one or more variables associated with the second cellular unit at each of the second plurality of different times. The method further includes correlating one of the predetermined amount of hypoxia and the predetermined rate of oxygen consumption in the first supporting medium with at least two of the other one of the predetermined amount of hypoxia and the predetermined rate of oxygen consumption in the first supporting medium, the values for the one or more variables associated with the first supporting medium, the values for the one or more variables associated with the first cellular unit and the first plurality of different times to generate a first multi-dimensional surface. The method further includes correlating one of the predetermined amount of hypoxia and the predetermined rate of oxygen consumption in the second supporting medium with at least two of the other one of the predetermined amount of hypoxia and the predetermined rate of oxygen consumption in the second supporting medium, the values for the one or more variables associated with the second supporting medium, the values for the one or more variables associated with the second cellular unit and the second plurality of different times to generate a second multi-dimensional surface. The method further includes identifying differences between the first multi-dimensional surface and the second multi-dimensional surface.

A method for assessing an effect on a cellular unit of an organism in accordance with another embodiment includes providing a first aliquot of a first sample including a first cellular unit not subject to the effect in a first supporting medium in a first hermetically sealed container. The method further includes providing a first aliquot of a second sample including a second cellular unit subject to the effect in a second supporting medium in a second hermetically sealed container. The method further includes deoxygenating the first supporting medium and the second supporting medium to induce at least one of a predetermined amount of hypoxia and a predetermined rate of oxygen consumption in the first supporting medium and in the second supporting medium. The method further includes determining, during deoxygenation of the first supporting medium, values for one or more variables associated with the first supporting medium at each of a first plurality of different times and/or values for two or more variables associated with the first cellular unit at each of the first plurality of different times. The method further includes determining, during deoxygenation of the second supporting medium, values for one or more variables associated with the second supporting medium at each of a second plurality of different times and/or values for two or more variables associated with the second cellular unit at each of the second plurality of different times. The method further includes correlating values for a first variable associated with first cellular unit, values for a second variable associated with the first cellular unit and at least one of the values for a first variable associated with the first supporting medium and the first plurality of times to generate a first multi-dimensional surface. The method further includes correlating values for a first variable associated with second cellular unit, values for a second variable associated with the second cellular unit and at least one of values for a first variable associated with the second supporting medium and the second plurality of times to generate a first multi-dimensional surface. The method further includes identifying differences between the first multi-dimensional surface and the second multi-dimensional surface.

A method for assessing an effect on a cellular unit of an organism in accordance with another embodiment includes providing a first aliquot of a first sample including a first cellular unit not subject to the effect in a first supporting medium in a first hermetically sealed container. The method further includes providing a first aliquot of a second sample including a second cellular unit subject to the effect in a second supporting medium in a second hermetically sealed container. The method further includes deoxygenating the first supporting medium and the second supporting medium to induce at least one of a first predetermined amount of hypoxia and a first predetermined rate of oxygen consumption in the first supporting medium and in the second supporting medium. The method further includes determining, during deoxygenation of the first supporting medium, a value for at least one variable associated with the first cellular unit at each of a first plurality of different times. The method further includes determining, during deoxygenation of the second supporting medium, a value for at least one variable associated with the second cellular unit at each of a second plurality of different times. The method further includes providing a second aliquot of the first sample including a third cellular unit not subject to the effect in a third supporting medium in a third hermetically sealed container. The method further includes providing a second aliquot of the second sample including a fourth cellular unit subject to the effect in a fourth supporting medium in a fourth hermetically sealed container. The method further includes deoxygenating the third supporting medium and the fourth supporting medium to induce at least one of a second predetermined amount of hypoxia and a second predetermined rate of oxygen consumption in the third supporting medium and in the fourth supporting medium. The method further includes determining, during deoxygenation of the third supporting medium, a value for at least one variable associated with the third cellular unit at each of a third plurality of different times. The method further includes determining, during deoxygenation of the fourth supporting medium, a value for at least one variable associated with the fourth cellular unit at each of a fourth plurality of different times. The method further includes correlating the at least one of the first predetermined amount of hypoxia and the first predetermined rate of oxygen consumption with the values for the at least one variable associated with the first cellular unit and the first plurality of different times and correlating the at least one of the second predetermined amount of hypoxia and the second predetermined rate of oxygen consumption with the values for the at least one variable associated with the third cellular unit and the third plurality of different times to generate a first multi-dimensional surface. The method further includes correlating the at least one of the first predetermined amount of hypoxia and the first predetermined rate of oxygen consumption with the values for the at least one variable associated with the second cellular unit and the second plurality of different times and correlating the at least one of the second predetermined amount of hypoxia and the second predetermined rate of oxygen consumption with the values for the at least one variable associated with the fourth cellular unit and the fourth plurality of different times to generate a second multi-dimensional surface. The method further includes identifying differences between the first multi-dimensional surface and the second multi-dimensional surface.

A system and method for assessing an effect on a cellular unit of an organism in accordance the present teachings represent an improvement as compared to conventional systems and methods. The system and method enable assessment of an effect at varying levels of hypoxia and rates of oxygen consumption and also under both equilibrium and non-equilibrium conditions to more accurately reflect in vivo conditions.

The foregoing and other aspects, features, details, utilities, and advantages of the present teachings will be apparent from reading the following description and claims, and from reviewing the accompanying drawings.

BRIEF DESCRIPTION OF THE DRAWINGS

FIGS. 9A-9B are contour maps illustrating sections of multi-dimensional surfaces correlating values for time, the rate of deoxygenation of a supporting medium, and erythrocyte sickling for multiple aliquots of sample subject to an effect (FIG. 9A) and a sample not subject to an effect (FIG. 9B) obtained from deoxygenation of the aliquots to the same predetermined amount of hypoxia, but at different predetermined rates of hypoxia.

FIG. 10C is a contour maps illustrating the differences between FIGS. 10A-10B.

DETAILED DESCRIPTION OF THE INVENTION

Figure 1:
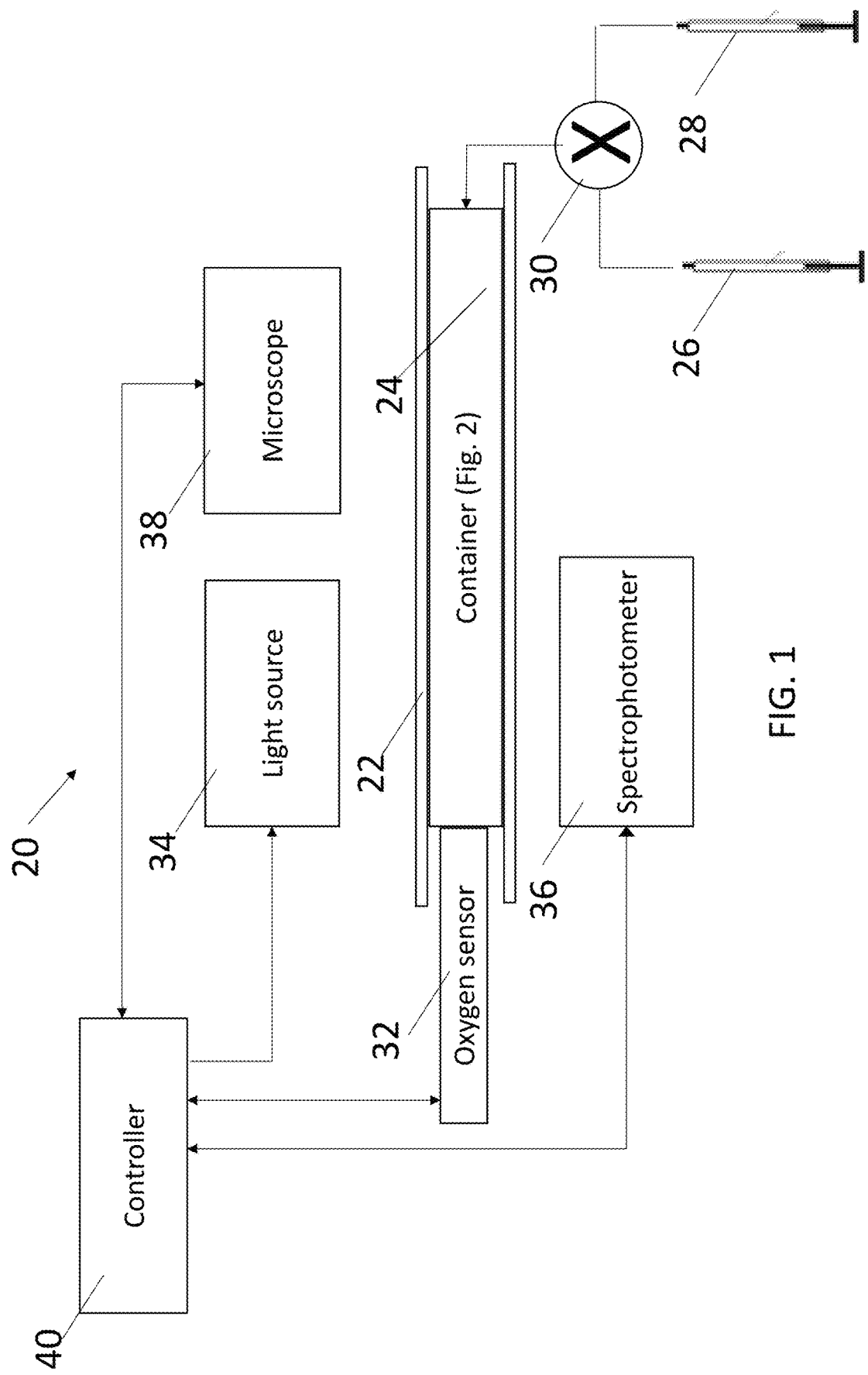
FIG. 1 is a schematic drawing of a system in accordance with one embodiment of the invention.

Referring now to the drawings wherein like reference numerals are used to identify identical components in the various views, FIG. 1 illustrates one embodiment of a system 20 for assessing an effect on a cellular unit of an organism in accordance with the present teachings. The effect could be a treatment, such as drug, a therapy (e.g., blood transfusion) or a change in diet or lifestyle. The effect could be the presence of a disease (e.g., as compared to the absence of a disease) or a pathology of a disease such a certain severity of the disease or occurrence of a symptom of the disease. The effect could be the passage of time. Although several exemplary effects have been identified herein, it should be understood that the cellular units of an organism may be subject to a wide variety of potential effects. The organism may comprise a human, but may alternatively comprise any other organism made up of cells. The term "cellular unit" as used herein refers to a cell and/or to a component of a cell. Therefore, for example, cellular unit may refer to a red blood cell (RBC), or erythrocyte, or to an individual component of an erythrocyte such as a hemoglobin (Hb) molecule. The embodiments of the system 20 and method described and illustrated herein are intended for use in assessing effects on erythrocytes and Hb molecules within erythrocytes and, in particular, for evaluation of the impact of sickle cell disease (SCD), SCD pathology, and SCD treatments on erythrocytes and Hb molecules. It should be understood, however, that systems and methods in accordance with the teachings herein may be applied for use with a variety of cellular units and organisms and to assess a variety of potential effects on such cellular units. System 20 is intended for use in research and testing, but is configured to have a relatively small footprint such that it is also capable of use at point of care locations such as a physician's office or a patient's residence. System 20 is also intended to be relatively inexpensive and simple to use such that it can be used in locations with limited infrastructure. System 20 may include means, such as a test stand 22, for supporting a container 24 that is used to hold a sample, or an aliquot of a sample, including one or more cellular units within a supporting medium and is described in greater detail hereinbelow. It should be understood that the configuration of test stand 22 will depend upon the configuration of container 24 as well as the surrounding equipment used to agitate the sample and take measurements of the sample. In accordance with various embodiments of the invention, system 20 may further include means, such as syringes 26, 28, for introducing cellular units, supporting mediums, and other materials into container 24, a mixer 30 for pre-mixing materials received from syringes 26, 28, an oxygen sensor 32, a light source 34, a spectrophotometer 36, a microscope 38, and a controller 40.

Syringes 26, 28 are provided to introduce various materials to container 24. In accordance with one embodiment, syringes 26, 28 may be configured to introduce a reaction substrate and a reaction enzyme, respectively, into container 24 to generate a reaction within container 24 and deoxygenate elements of a sample contained within container 24 such as one or more cellular units and/or a supporting medium for the cellular units. Syringes 26, 28 may also be used, however, to introduce elements of the sample to container 24 and may be used to introduce multiple materials at once (e.g., a sample and one of the reaction substrate and reaction enzyme). In some embodiments, system 20 may implement a stop flow technique in which introduction of material from syringes 26, 28 displaces pre-existing contents within container 24 (e.g., from a prior assessment) until a predetermined volume of the contents is removed from the container 24 as indicated by a measurement device such as a plunger of another syringe (not shown) acting on a switch (not shown).

Mixer 30 is a component that may be provided to mix the contents of syringes 26, 28 prior to introduction to container 24 in certain embodiments. Mixer 30 may also be used to insure even distribution of materials and produce a homogenous mixture of materials within container 24. Mixer 30 is conventional in the art.

Oxygen sensor 32 is provided to measure the oxygen concentration in the supporting medium for the cellular units within the sample in container 24. Sensor 32 generates output signals indicative of the oxygen concentration in the supporting medium and provides the signals to controller 40 for use in determining levels of hypoxia in the supporting medium and rates of deoxygenation in the supporting medium. Sensor 32 may comprise the sensor offered for sale by PyroScience GmbH under the model number OXROB 10.

Light source 34 is provided to generate and direct light into the sample within container 24. Light source 34 may comprise one or more light emitting didoes (not shown) that generate radiation that passes through the sample within container 24. Light source 34 may be controlled in response to control signals from controller 40.

Spectrophotometer 36 is provided to measure deoxygenation of cellular units within container 24. Spectrophotometer 36 may also be provided to measure the oxygen concentration in the supporting medium for the cellular units in container 24 as an alternative to use of oxygen sensor 32. Spectrophotometer 36 analyzes the sample in container 24 by recording and measuring spectral components of electromagnetic radiation such as light passing through the sample from light source 34. Spectrophotometer 36 generates and provides output signals to controller 40 which may then determine the rate of deoxygenation in cellular units within container 24, and optionally, the level of hypoxia and rate of oxygen consumption in the supporting medium within container 24 responsive to those signals. In accordance with one embodiment of the invention, the cellular units comprise Hb molecules. Spectrophotometer 36 generates signals indicative of the rate of deoxygenation of the Hb molecules based on differences in light absorbance between oxygenated Hb and deoxygenated Hb in the visible range (500-700 nm) or in the ultraviolet range (400-450 nm). In one embodiment, spectrophotometer 36 may measure absorbance in the ultraviolet range, to validate or calibrate for the reactivity of an enzymatic oxygen scrubbing system (e.g., using the change in absorbance at 290 nm to monitor for the conversion of a protocatechuic acid (PCA) substrate to the product (p-carboxy-cis, cis-muconate) in the cause of catalysis.

Microscope 38 is provided to magnify a view of the sample. In accordance with certain embodiments, microscope 38 is provided to magnify a view of a sample including whole blood or erythrocyte suspensions to allow optical assessment of the sickling of erythrocytes within the sample and, in particular, the number of sickled erythrocytes and/or the proportion of sickled erythrocytes relative to unsickled erythrocytes and/or the different types of erythrocyte sickling (e.g., crescent, holly leaf, granular) and the numbers/proportions of each type. Microscope 38 may also be provided to evaluate other morphological changes in erythrocytes such as crenation. Microscope 38 may include a camera or similar image capture device and a memory for storage of captured images and may transmit the images or information obtained from the images to controller 40. The number of sickled erythrocytes and/or the proportion of sickled erythrocytes relative to unsickled erythrocytes may be determined manually through review of the images. Alternatively, this information could be determined automatically by microscope 38 and/or controller 40 through appropriate object recognition software.

Controller 40 controls the operation of oxygen sensor 32, light source 34, spectrophotometer 36 and, in certain embodiments, microscope 38 and is configured to receive and process signals generated by oxygen sensor 32, spectrophotometer 36 and, in certain embodiments, microscope 38. Controller 40 may comprise a programmable microprocessor or microcontroller or may comprise an application specific integrated circuit (ASIC). Controller 40 may include a central processing unit (CPU). Controller 40 may also include a memory and an input/output (I/O) interface through which controller 40 may receive a plurality of input signals including those generated by oxygen sensor 32, spectrophotometer 36, microscope 38 and those entered through conventional I/O devices such as keyboards, touch screen displays, etc. and transmit a plurality of output signals including those used to control oxygen sensor 32, light source 34, spectrophotometer 36 and, in certain embodiments, microscope 39.

Figure 2:
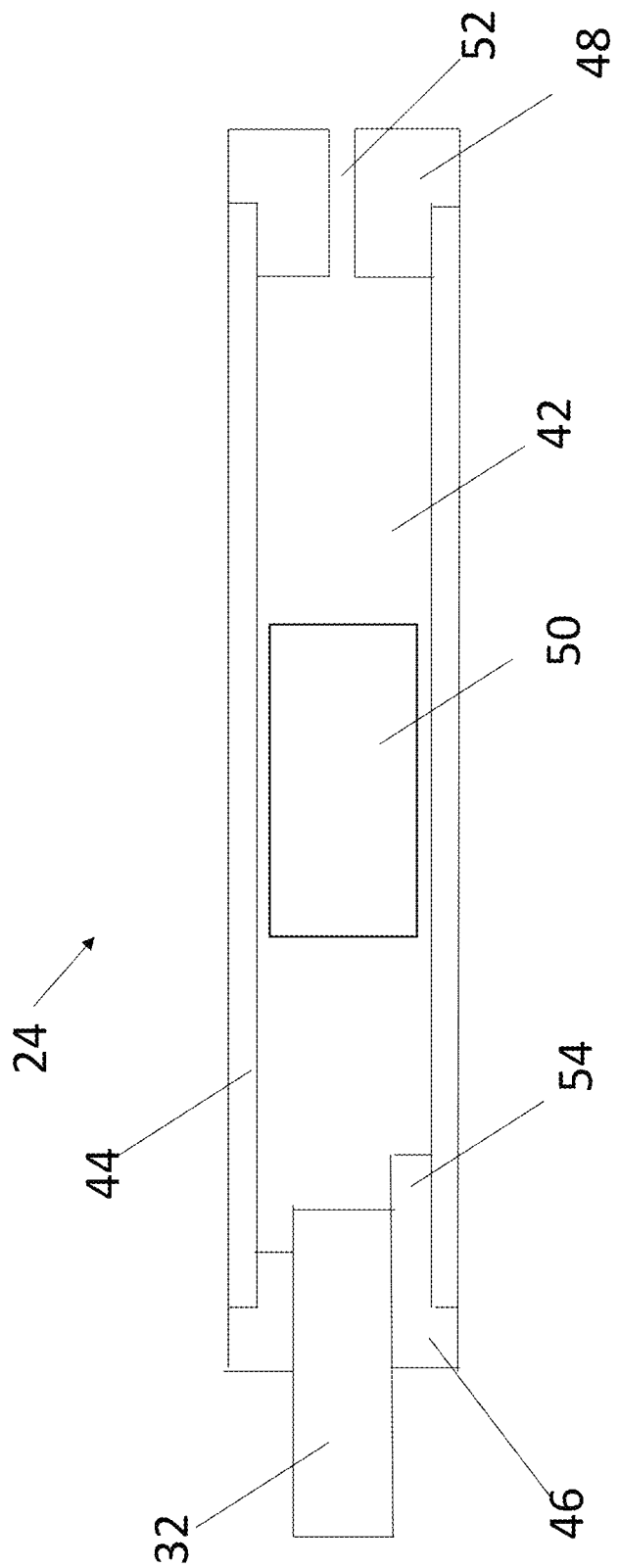
FIG. 2 is a drawing of a sample container for use in the system of FIG. 1.

Referring now to FIG. 2, one embodiment of a container 24 for use in system 20 will be described in greater detail. Container 24 is configured to receive and contain a sample 42, or an aliquot of sample 42, including one or more cellular units within a supporting medium. In accordance with certain embodiments, sample 42 may include whole blood in which erythrocytes and other cellular units are supported within blood plasma. Sample 42 may alternatively comprise hemolyzed blood (whole blood lysate) containing at least some ruptured erythrocytes and extracellular Hb molecules supported within blood plasma and buffer solutions. Sample 42 may alternatively comprise only erythrocytes or only extracellular Hb molecules within a buffer solution such as phosphate-buffered saline (PBS) or Hanks' Balanced Salt Solution (HBSS) supplemented by 4-(2-hydroxyethyl)-1-piperazineethanesulfonic acid (HEPES) or generic phosphate buffer. Although each of the described samples relates to erythrocytes and components of erythrocytes, it should again be understood that systems and methods in accordance with the teachings herein could be applied to a variety of different cellular units forming various types of tissues and organs in organisms. Container 24 is hermetically sealed and may be supported by a cartridge (not shown) configured for mounting on test stand 22. Container 24 may include a tube 44, end caps 46, 48 and a bead 50.

Tube 44 may be transparent to allow evaluation of sample 42 using spectrophotometer 36 and microscope 38. Tube 44 may be made from a flexible plastic material and may comprise tubing sold under the registered trademark "TYGON" by Saint-Gobain Performance Plastics Corporation.

End caps 46, 48 are configured to hermetically seal either end of tube 44. End cap 46 may defines a bore configured to receive oxygen sensor 32 and may be molded around oxygen sensor 32. End cap 48 may define one more capillaries 52 through which the materials, such as sample 42 or enzymes used to deoxygenate sample 42 may be introduced into container 24 using, for example, syringes 26, 28. In certain embodiments, a capillary 52 or an interior surface of tube 44 may be coated with an endothelial substrate configured to interact with the cellular units such as the cell adhesion molecules/proteins VCAM-1 or P-Selectin for the purpose of separating cells with greater adhesion to the substrate. Cells that do not adhere to the substrate may be removed through capillaries 52 prior to evaluation of the cells adhered to the substrate. Capillaries 52 in end cap 46 or end cap 48 may further be used to remove materials from container 24 including in embodiments in which a stopped flow technique is used to introduce material to container 24.

Bead 50 may be provided for use in lysis of cells in sample 42. Bead 50 may comprise a magnetic bead that may be moved within the container 24 under the influence of electromagnets (not shown). Oscillation of bead 50 induces flows through the annular gap between the bead 50 and container wall with the speed of the flow regulated through the size of the gap and bead oscillation parameters (intensity, frequency). Flow velocity and type (turbulent, laminar) is the defining parameter for flow induced cell stress, and a stress with a predefined shear rate can be achieved using methods well known in the art. That allows, when necessary, to induce shear stress of desired intensity and duration while the sample 42 is at a desired level of hypoxia. End cap 46 may define an extension 54 that extends beyond the end of oxygen sensor 32 and is configured for contact with bead 50 to limit movement of bead 50 and prevent contact between oxygen sensor 32 and bead 50.

Figure 3:
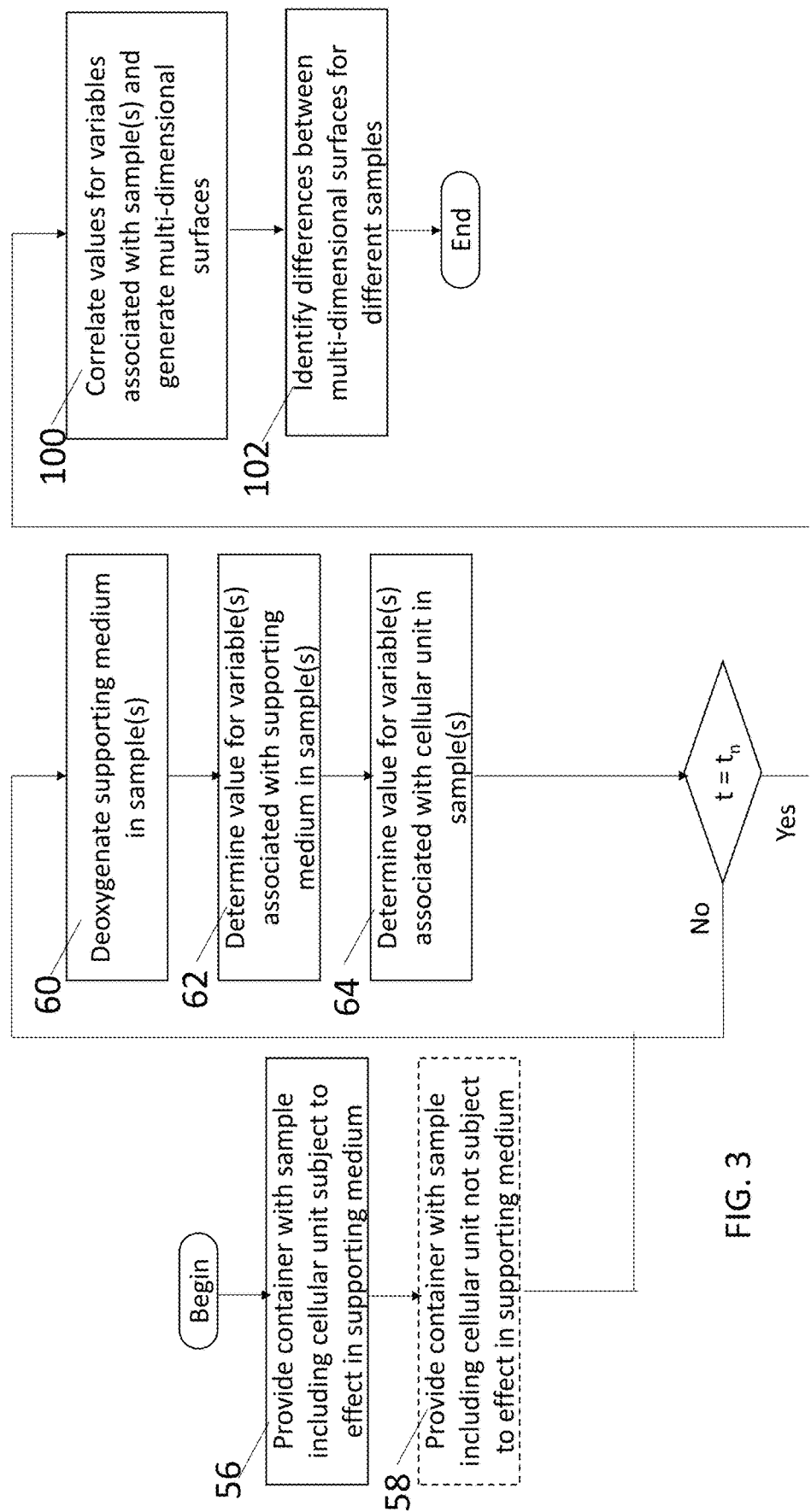
FIG. 3 is a flowchart illustrated a method in accordance with various embodiments of the invention.

Referring now to FIG. 3, various embodiments of a method for assessing an effect, such as a treatment, disease, or the passage of time on a cellular unit of an organism in accordance with the present teachings will be described. The method may begin with the step 56 of providing an aliquot of a sample A including one or more cellular units that are subject to the effect in a supporting medium in a hermetically sealed container 14. In some embodiments, the method may further include the step 58 of providing an aliquot of a sample B including one or more cellular units that are not subject to the effect in a supporting medium in another hermetically sealed container 14. For purposes of comparison, the type of supporting mediums in each of samples A and B is preferably the same. The type of cellular unit in each of samples A and B will also preferably be the same (with the only difference being that the cellular units in sample A are subject to the effect while the cellular units in the sample B are not subject to the effect), but in certain embodiments the samples A and B may include the same type of cellular units, but with differences other than the effect, or even different types of cellular units. Referring to FIGS. 1-2, the aliquots of samples A and B may be introduced to the containers 24 using syringes 26, 28 and, optionally, mixer 30, or in other embodiments through capillaries 52 in the end cap 48 of each container 24. In some embodiments, portions of the aliquots of samples A and/or B may be removed prior to subsequent steps in the method. For example, in some embodiments, a portion of container 24 may be coated with an endothelial substrate such as cell adhesion molecules/proteins VCAM-1 or P-Selectin for the purpose of separating cells with greater adhesion to the substrate from samples containing erythrocytes. The containers 24 may then be washed with buffer to eliminate non-adhering cells prior to performing subsequent steps in the method.

Referring again to FIG. 3, the method may continue with the step 60 of deoxygenating the supporting medium in the aliquot of sample A and, in certain embodiments, the supporting medium in the aliquot of sample B to induce at least one of a predetermined amount of hypoxia and a predetermined rate of oxygen consumption in each of the supporting mediums. Deoxygenation of the supporting mediums in the aliquots of samples A and B may occur at the same or different times. Deoxygenation may be performed through enzymatic catalysis using enzymatic oxygen scavengers/scrubbers such as glucose oxidase or pyranose oxidase. In a preferred embodiment, deoxygenation is performed through enzymatic catalysis using a reaction substrate comprising protocatechuic acid (PCA) and a reaction enzyme comprising protocatechuate-2,3-dioxygenase (PCD). PCD catalyzes the conversion of PCA and oxygen in the supporting medium in a 1:1 stoichiometry into β-carboxy-cis, cis-muconic acid (CMA). The use of PCA/PCD has a number of advantages relative to other enzymatic catalysis methods and other methods of deoxygenation. The use of PCA/PCD also does not generate any reactive oxygen species such as peroxide or superoxide during the catalyzed reaction with oxygen and does not interfere with independently produced reactive oxygen species (e.g., due to the presence of antioxidants like catalase, as used in some other enzyme-based systems). The use of PCA/PCD can achieve greater levels of hypoxia in the samples relative to some other methods. The use of PCA/PCD can also achieve specific levels of hypoxia as opposed to proceeding to complete hypoxia as in other methods thereby allowing simulation of more specific conditions (e.g., for a particular organ or particular level of hypoxia). Most importantly, the use of PCA/PCD allows accurate control of the rate of oxygen consumption in both the supporting medium and, as a result, the rate of deoxygenation of Hb in embodiments where the cellular unit comprises erythrocytes or extracellular Hb. Conventional methods of deoxygenation assume equilibrium or quasi-equilibrium conditions in which, for example, the rate of Hb deoxygenation occurs more slowly than the rate of oxygen consumption in the supporting medium. These equilibrium conditions may not exist, however, in vivo. Erythrocytes are exposed to oxygen from the lungs and to hypoxia in other organs for relatively short periods (e.g., the erythrocytes reside in lungs for about 250 ms dependent on blood pressure, heart rate, etc.) and move between the lungs and other organs relatively quickly. In particular, erythrocytes are exposed to a hypoxic environment, offload a portion of the oxygen carried by the Hb and leave through venous circulation during a capillary transit time of about in about 150-700 ms depending on blood flow rates. Conventional methods relying on oxygen diffusion for deoxygenation, for example, may need as much as 20-30 minutes per measurement thereby simulating conditions very different from physiological conditions.

When using PCA/PCD, step 60 may include several substeps. First, one of the reaction substrate (i.e., PCA) and the reaction enzyme (i.e., PCD) may be introduced into the containers 24 containing the aliquots of samples A, B. The substance may be introduced to a container 24 already containing an aliquot of sample A or B through a capillary 52 in container 24. Alternatively, the substance may be premixed with the sample A or B or a portion or aliquot of the sample A or B prior to introduction of the mixture into the container 24 through capillary 52. Next, the other of the reaction substrate and reaction enzyme may be introduced into the containers 24 containing the aliquots of samples A, B. The substance may again be introduced to the container 24 through a capillary 52 in container 24. In an alternative embodiment, the substance may again be premixed with sample A or B or a portion or aliquot of sample A or B (e.g., using mixer 30). In certain embodiments, separate portions or aliquots of each sample A or B are premixed with the reaction substrate and with the reaction enzyme and introduced to the corresponding container 24 at substantially the same time. The amount of PCA and PCD introduced to the container 24 may be calculated to achieve a predetermined effect in the sample 42 during the reaction between the PCA, PCD and oxygen. In particular, the amount of PCA may be selected to induce a predetermined amount of hypoxia in the sample 42. The predetermined amount may correspond to a particular physiological effect (e.g., a level hypoxia resulting from physical exertion or being due to a particular elevation). The predetermined amount may alternatively correspond to a level found in a particular organ with a living body. The predetermined amount may alternatively correspond to a level corresponding a pathological condition. In accordance with one embodiment, the amount corresponds to a level associated with sickle cell disease (SCD). The amount of PCD may alternately, or in addition, be selected to induce a predetermined rate of oxygen consumption in the sample 42. The predetermined rate may again correspond to a particular physiological effect or rate corresponding to a particular organ with a living body or pathological condition. In accordance with one embodiment, the rate corresponds to a level associated with sickle cell disease (SCD) and, in particular, may correspond to a rate of development of a predetermined sickled red blood cell morphological form. A predetermined rate of oxygen consumption as used herein should be understood as a predefined rate of change in partial oxygen pressure due to oxygen consumption in a medium in a sample with no oxygen diffusion into such medium from either the environment outside the container containing the sample or from components contained within the sample such as, for example, erythrocytes or extracellular hemoglobin. Further information regarding the deoxygenation of the samples A, B through the use of PCA and PCD may be found in Applicant's pending U.S. patent application Ser. No. 17/016,849 titled "Method for Assessing Effects of Hypoxia on Tissues," the entire disclosure of which is incorporated herein by reference.

As step 60 proceeds, the supporting medium for the aliquot of sample A and, in certain embodiments, the supporting medium for the aliquot of sample B will reach increasingly greater levels of hypoxia. Referring again to FIG. 3, the method may further include several steps 62, 64 in which values for one or more different variables associated with the aliquots for sample A and/or B are obtained at a plurality of different times $t_1 \ldots t_n$ corresponding to increasing levels of hypoxia in the supporting medium(s) for the aliquots of samples A, B. In some embodiments, the values for each variable associated with a given sample may be obtained contemporaneously. In other embodiments, the values for some variables may be obtained at the indicated time $t_1 \ldots t_n$ while the values for other variables are obtained at a later time based on information captured at the indicated time $t_1 \ldots t_n$. Regardless, the performance of steps 62, 64 ultimately results in a plurality of sets of corresponding values for different variables associated with the aliquot of a sample with the values in each set linked together by a time $t_1 \ldots t_n$ that in turn may correspond to increasing levels of hypoxia in the supporting medium for the aliquot of the sample. In certain embodiments in which values for variables associated with multiple samples (e.g., A and B) are obtained for eventual comparison, it should be understood that each time $t_1 \ldots t_n$ for sample A may not be identical to a corresponding time $t_1 \ldots t_n$ for sample B because samples A, B may be examined at different times and over different lengths of time. However, each time $t_1 \ldots t_n$ associated with sample A will preferably correspond to each time $t_1 \ldots t_n$ associated with sample B in some manner. For example, steps 62, 64 may be performed when the supporting mediums in samples A, B reach corresponding levels of hypoxia. In some embodiments, step 60 may be performed in a step-like manner such that the supporting medium(s) reach one level of hypoxia that is maintained for a period of time before subsequently proceeding to a greater level of hypoxia that is maintained for a period of time and so on. The use of PCA and PCD as described can facilitate this step-like increase in the level of hypoxia. In these embodiments, performance of steps 62, 64 may obtain values at times during the periods at which the levels of hypoxia in the supporting medium(s) are being maintained. In other embodiments, step 60 may proceed with a continuous increase (e.g., linearly, logarithmically, etc.) in the level of hypoxia in the supporting medium(s).

During step 62, one of the variables associated with the supporting mediums for samples A and/or B that may be determined may comprise a level of hypoxia in the supporting medium(s). As mentioned above, the level of hypoxia in a supporting medium may be determined using oxygen sensor 32. Alternatively, when PCA and PCD are used to deoxygenate the supporting medium in step 60, the level of hypoxia may be determined using light source 34 and spectrophotometer 36 by monitoring spectrophotometric changes resulting from the conversion of PCA to β-carboxy-cis, cis-muconic acid (CMA) and calculating the amount of consumed oxygen based on the amount of PCA converted to CMA. Such an approach may be used, for example, for in-situ calibration of PCD activity.

Another of the variables associated with the supporting mediums for samples A and/or B that may be determined may comprise the rate of deoxygenation in the supporting medium(s). As mentioned above, the level of hypoxia in a supporting medium may be determined using oxygen sensor 26. In certain embodiments when PCA and PCD are used to deoxygenate the supporting medium, the level of hypoxia in a supporting medium may be determined using light source 34 and spectrophotometer 36 and controller 40. Alternatively, the amount of PCD could be calibrated to induce a known rate of oxygen consumption between each of times $t_1 \ldots t_n$ so that if the total amount of oxygen is known and the kinetics of oxygen equilibrium between the medium and oxygen bound to cellular elements like hemoglobin are known, the rate of deoxygenation of the medium can be determined. Controller 40 may determine the rate of deoxygenation in the supporting medium by comparing the level of hypoxia in the supporting medium at time $t_x$ with the level of deoxygenation in the supporting medium at time $t_{x-1}$.

During step 64, values for one or more variables associated with the cellular unit in the supporting medium for sample A and, in certain embodiments, one or more variables associated with the cellular unit in the supporting medium for sample B may be determined. The type and number of variables will depend on the type of cellular unit and the information sought to be obtained. In accordance with one embodiment of the invention in which the cellular units comprise erythrocytes or cell-free Hb, one of the variables may comprise the rate of deoxygenation of either intracellular or extracellular Hb. The rate of deoxygenation in Hb may be determined using light source 34 and spectrophotometer 36 and controller 40. Controller 40 may determine the rate of deoxygenation of Hb by comparing the level of deoxygenation in Hb at time $t_x$ with the level of deoxygenation in Hb at time $t_{x-1}$.

In accordance with certain embodiments of the invention, the use of PCA and PCD in step 60 enables relatively precise control and alteration of the rate of oxygen consumption in supporting medium and by extension of the rate of deoxygenation of the supporting medium which may affect the rate and the amount of deoxygenation of Hb in erythrocytes (e.g., by accelerating or decelerating the rate of change of oxygen in the medium and thus accelerating or decelerating the rate of oxygen release and the amount of oxygen released from Hb during its deoxygenation) to make the process approaching the kinetics more typical for in vivo conditions. The use of PCA and PCD to induce deoxygenation in step 60 may provide a relatively fast rate of deoxygenation in the supporting medium and, in particular, a rate of deoxygenation in the supporting medium that is greater than a rate of oxygen release from Hb and of the change in the deoxygenation of Hb. In SCD, deoxygenation of the supporting medium (blood plasma) results in deoxygenation of HbS which in turn results in HbS polymerization and, ultimately, morphological changes in erythrocytes, including cell sickling. Conventional systems and methods for assessing effects on erythrocytes and Hb assess effects under equilibrium or quasi-equilibrium conditions, where the medium deoxygenation proceeds more slowly than the rates of Hb deoxygenation, consequent HbS polymerization and the follow-up morphological change, including cell sickling. Therefore, conventional systems and methods generate conditions that allow for equilibration between medium oxygen concentration, Hb deoxygenation, polymerization and cell sickling with equilibrium reached at each stage of the process. While these assays are useful for simulating longer term effects of SCD, these systems and method are unable to simulate in vivo conditions for SCD in which reactions between (i) decreases in oxygen concentration and hemoglobin deoxygenation, (iii) hemoglobin deoxygenation and hemoglobin polymerization and (iii) hemoglobin polymerization and changes in cell morphology do not proceed in equilibrium. As noted above, erythrocytes are exposed to oxygen from the lungs and to hypoxia in other organs for relatively short periods and move between the lungs and other organs relatively quickly. In accordance with one aspect of the teachings herein, the deoxygenation of the supporting medium in step 60 may be performed to establish a rate of deoxygenation in the supporting medium that is either slower than the rate of the change of one or more variables associated with the cellular unit in the supporting medium, resulting in an equilibrium or quasi-equilibrium measurements, or faster than the rate of the change of one or more variables associated with the cellular unit in the supporting medium, resulting in "kinetic" measurements. As a result, where the cellular unit comprises an erythrocyte or Hb, the rate of deoxygenation of Hb (as well as the rate of HbS polymerization and erythrocyte sickling) may be made slower than the rate of deoxygenation in the supporting medium to approximate non-equilibrium or kinetic conditions that better simulate in vivo conditions. Under such conditions, with supporting medium and Hb deoxygenation states being out of equilibrium, a delay in Hb deoxygenation, as compared to medium deoxygenation will be observed. If no more oxygen consumption occurred, medium and Hb deoxygenation would eventually reach, through oxygen exchange, an equilibrium defined, in part, by hemoglobin affinity to oxygen. Alternatively, if oxygen remains to be consumed quickly, for example, through PCD enzymatic reaction with PCA and oxygen, an equilibrium between medium deoxygenation and oxygen bound to Hb may not be reached if the oxygen consumption is fast enough and the time for observation is sufficiently short. That would be a set of conditions that could simulate the processes occurring in vivo. Similarly, the systems and methods disclosed herein may facilitate conditions under which the rate of HbS polymerization and erythrocyte sickling may be either slower than the rate of HbS deoxygenation and the rate of erythrocyte sickling may be either slower than the rate of HbS polymerization. Under such conditions, HbS polymerization and erythrocyte sickling may exhibit a delay in developing as compared with Hb deoxygenation. Such a delay between Hb deoxygenation and erythrocyte sickling may stimulate the delay that can occur in vivo with erythrocytes traversing microcapillary network with the transition rates being shorter than the delay between Hb deoxygenation and Hb polymerization and RBC sickling.

The values obtained in steps 62, 64 may be used in various embodiments to generate a variety of information regarding each sample and the cellular units in each sample. The values may be used to generate information including, for example, the change in oxygen content over time for the supporting medium or the oxygen affinity of the cellular unit. Where the cellular units comprise erythrocytes or Hb, the values may further be used to generate standard oxygen dissociation curves and to obtain standard clinical parameters from such curves such as P50 (the partial pressure of oxygen ($PO_2$) in the supporting medium at which Hb is 50 percent saturated with oxygen or at which 50% of Hb is deoxygenated).

Figure 4:
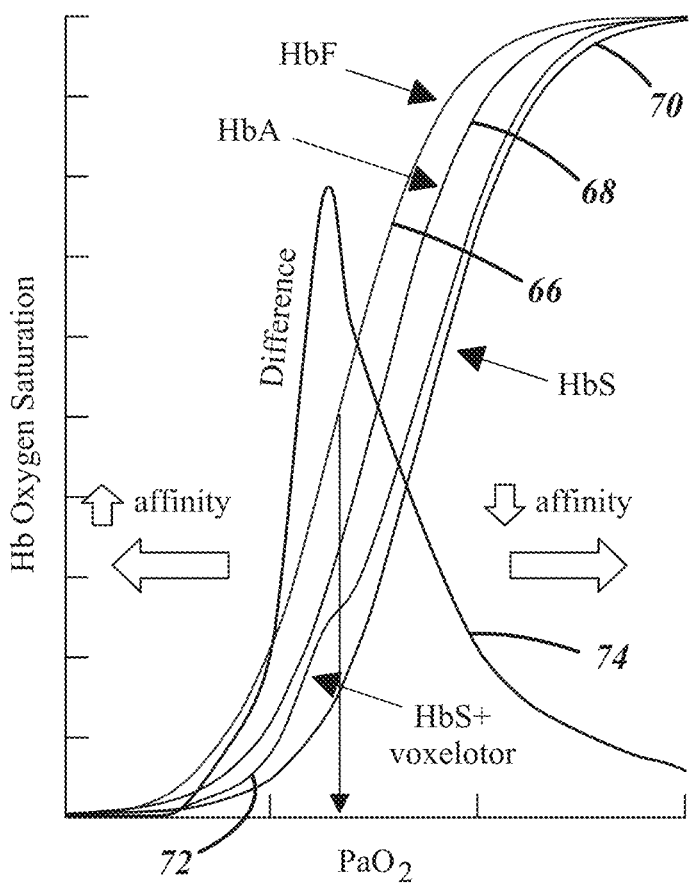
FIG. 4 is a graph illustrating a level of oxygen saturation for hemoglobin as a function of the partial pressure of oxygen in a supporting medium for several different types of hemoglobin and for hemoglobin in association with a hemoglobin-modifying drug.

Referring to FIG. 4, several exemplary oxygen dissociation or HB deoxygenation curves 66, 68, 70, are illustrated demonstrating differences in oxygen affinity for fetal hemoglobin (HbF), adult hemoglobin (HbA) and sickled hemoglobin (HbS). As is evident from curves 66, 68, 70, the type of hemoglobin in a body impacts the level of hemoglobin oxygen saturation at different partial oxygen pressures ($PO_2$). For example, HbF has increased oxygen affinity as compared to HbA and offloads oxygen less quickly in hypoxic environments. As a result, the oxygen saturation of HbF is greater than HbA at lower $PO_2$ and the curve 66 for HbF is leftward of the curve 68 for HbA. HbS has a reduced oxygen affinity relative to both HbF and HbA. As a result, the oxygen saturation for HbS is less than HbF and HbA at the same $PO_2$ and the curve 70 for HbS is rightward of the curves 66, 68 for HbF and HbA. The position of an Hb deoxygenation curve may also be impacted by a variety of physiological factors including, but not limited to, pH levels, temperature, and 2,3-DPG concentrations. In particular, decreases in pH levels, increases in temperature (which increase a body's metabolism and need for oxygen) and increase in 2,3-DPG concentrations (resulting from, for example, anemia, alkalosis, or chronic hypoxemia) all reduce hemoglobin oxygen affinity and shift a curve rightward. Conversely, increases in pH levels, decreases in temperature and decreases in 2,3-DPG concentrations (resulting from, for example, acidosis or administration of stored blood) will increase hemoglobin oxygen affinity and shift a curve leftward. The position of an Hb deoxygenation curve may also be impacted by various treatments. For example, in order to treat SCD, a variety of drugs have been developed that have the effect of moving a portion or all of curve 70 leftward in the drawing such that the oxygen saturation of an SCD patient's hemoglobin increases at lower $PO_2$. For example, hydroxyurea is sometimes used to increase the amount of HbF in a patient. Other drugs are used to affect aspects of erythrocyte metabolism such as 2,3-DPG concentration. The drug voxelotor, which is sold under the brand name "OXBRYTA" by Global Blood Therapeutics, Inc., binds to Hb and attempts to increase the oxygen affinity of the patient's Hb with the goal of delaying Hb deoxygenation, Hb polymerization and erythrocyte sickling to allow erythrocytes to flow through hypoxic environments before Hb polymerization and erythrocyte sickling can occur. Curve 72 illustrates Hb oxygen saturation levels at different $PO_2$ values for a patient with HbS using voxelotor while curve 74 illustrates the difference between the curves 70, 72. Various positions on these curves 66, 68, 70, 72, 74 may be used to assess an effect on an erythrocyte or Hb and, more generally, to evaluate a patient's condition or response to therapy. Positions on the curves 66, 68, 70, 72, 74 may also be used to optimize these assessments by, for example, identifying optimal target $PO_2$ levels for evaluating changes resulting from the effect. For example, the comparison between curves 70, 72 may be best where the difference between the two curves 70, 72 is greatest. Therefore, the deoxygenation step 60 may be configured in future iterations to achieve a particular $PO_2$ where the difference between the two curves 70, 72 is greatest.

Notably, Hb deoxygenation curves of the type shown in FIG. 4 are typically done base on a hemolyzed sample in which erythrocytes are lysed and Hb is found outside of the erythrocytes. The system and method disclosed herein may be used, however, on whole blood in which the erythrocytes are intact and Hb is still contained within the erythrocytes and at much higher concentrations as compared to a typical hemolyzed sample. Hb deoxygenation in whole blood (which better approximates in vivo conditions) may differ significantly from Hb deoxygenation in hemolyzed samples. In particular, Hb deoxygenation may be affected by oxygen diffusion across the erythrocyte membrane and within the erythrocytes. Hb deoxygenation may also be affected by Hb concentration which may be greater within erythrocytes than outside of erythrocytes as in hemolyzed samples. Hb deoxygenation may also be affected by intracellular Hb oxygen affinity modifiers including natural modifiers such as 2,3-Diphosphoglycerate (2,3-DPG) or artificial modifiers such as a drug (e.g., voxelotor).

In addition to standard oxygen dissociation or Hb deoxygenation curves, the information from steps 62, 64 may be used to generate curves of hemoglobin deoxygenation as a function of the deoxygenation rate of the medium. These curves may be used to assess potential deoxygenation rates for erythrocytes or Hb that encounter hypoxic conditions while in transit in blood circulation. In particular, when using PCA and PCD or other enzymatic systems to deoxygenate the supporting medium in step 60, relatively fast deoxygenation is enabled (e.g., on hundreds of millisecond time scale or potentially faster, depending on the enzyme activity with reported activity up to 130 $s^{-1}$, implying potential for medium deoxygenation at rates down to tens of milliseconds). Shorter deoxygenation times (faster deoxygenation rates) are more likely to approximate in vivo or physiological conditions.

In the embodiment described above, one potential variable associated with a cellular unit comprising an erythrocyte or Hb—the rate of deoxygenation of Hb—is described. Other variables associated with erythrocytes or Hb may also be determined in step 64 either as an alternative to, or in addition to, the rate of deoxygenation of Hb.

In one embodiment, the variable may comprise a change in the morphology of the cellular unit such as the number or percentage of sickled erythrocytes or even the number or percentage of a particular shape or morphological form of sickled erythrocytes. As mentioned above, these values can be obtained using microscope 38 and controller 40. One aspect of a system and method in accordance with the teachings herein is that the system and method provide information on why sickling has occurred. Systems and methods for identifying and counting sickled cells are known, but these conventional systems and method only provide information on the occurrence or extent of sickling and not why the sickling has occurred. About 3-7% of erythrocytes are irreversibly sickled in a typical SCD patient. Hemoglobin deoxygenation will induce reversible sickling in erythrocytes containing sickled hemoglobin (HbS) and in erythrocytes containing (i) both HbA and HbS, (ii) HbF and HbS or other hemoglobin forms comprising HB abnormal forms (C, D, E, O, thalassemia associated with changes in the globin part of Hb, etc.) or (iii) HbS treated with Hb modifying compounds (e.g., voxelotor), but at lower oxygen tensions relative to untreated cells with untreated HbS. In homozygous Sickle Cell Disease (HbSS autosomal recessive) HbS polymerization, which leads to erythrocyte sickling, occurs in response to HbS deoxygenation and can be affected by number of factors including actual Hb concentration, forms of Hb present inside the cells (e.g., HbF, HbA, HbS and others), temperature and other environmental factors affecting HbS nucleation including the presence of Hb modifying drugs that in addition to shifting the oxygen dissociation (Hb deoxygenation) curve may hinder polymer formation by either blocking binding sites or due to steric effects (e.g., with the drug stereoscopically destabilizing polymer formation). There is also a delay following HbS deoxygenation before HbS polymerization begins. This delay is of critical importance as it allows HbS containing cells to pass through hypoxic space (e.g., in organs) without polymerization and thus without sickling. On the other hand, upon reoxygenation, there is also a delay in polymer melting such that, once sickled, a reversibly sickled erythrocyte may take additional time before it will start de-sickling (polymer melting). The system and method described herein correlate information on the number and/or type of sickled cells with other information including, for example, the level of hypoxia in the supporting medium, the rate of oxygen consumption in the supporting medium, and the rate of deoxygenation of Hb to allow improved assessment of the conditions that result in sickling, the pathology of SCD and potential treatments.

Figure 5:
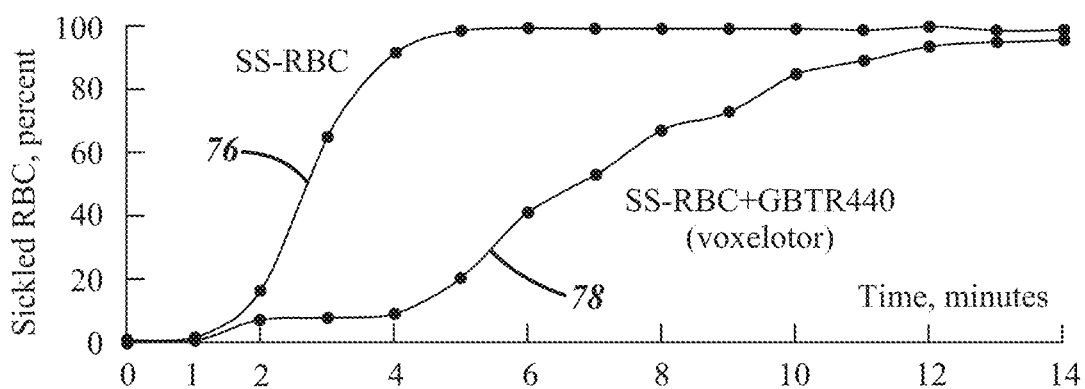
FIG. 5 is a graph illustrating a percentage of sickled erythrocytes over time for one sample that is exposed to a drug and one that is not.
Figure 6:
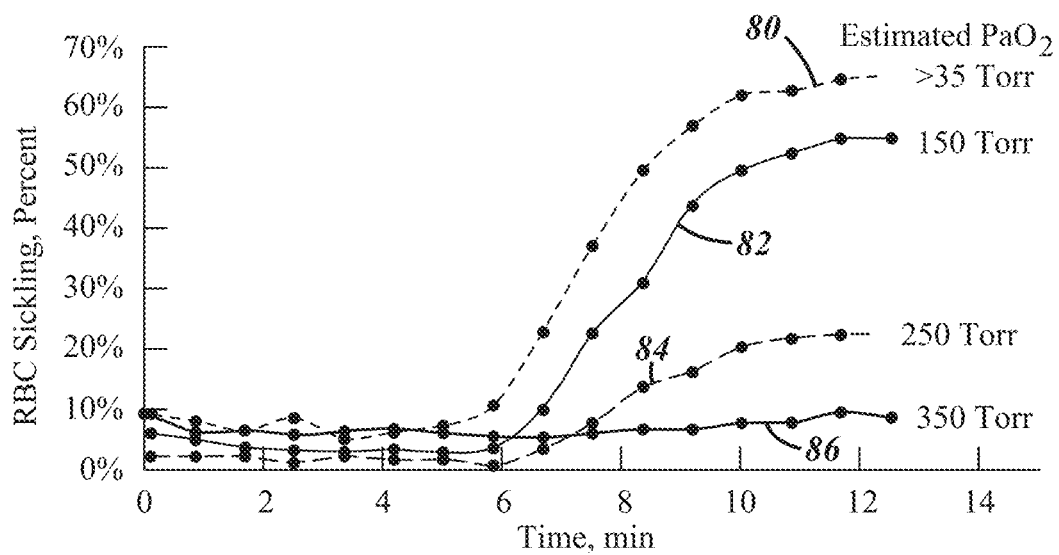
FIG. 6 is a graph illustrating a percentage of sickled erythrocytes over time for different samples of erythrocytes in which the supporting medium for the erythrocytes is exposed to different levels of hypoxia.

Referring to FIGS. 5-6, when one of the variables in step 64 comprises the number or percentage of sickled erythrocytes (or a particular shape or morphological form of sickled erythrocyte), the information may be used to generate information on the amount of sickling over time. FIG. 5 shows two curves 76, 78, illustrating the percentage of sickling of erythrocytes over time as a result of deoxygenation of two samples in the same manner (same erythrocyte-containing sample deoxygenated by the PCA/PCD system at the same rate of oxygen consumption), with curve 76 demonstrating a reduction in sickling, including a longer delay in sickling and slower erythrocyte sickling rate resulting from treatment with the drug voxelotor. FIG. 6 shows four curves 80, 82, 84, 86 illustrating the percentage of sickling of erythrocytes over time as a result of deoxygenation of the supporting medium in four aliquots of a sample to different levels of hypoxia with curve 80 illustrating the highest level of hypoxia and curve 86 illustrating the smallest level of hypoxia at the conclusion of enzymatic reaction of PCD with PCA an oxygen when PCA is fully consumed.

Figure 7:
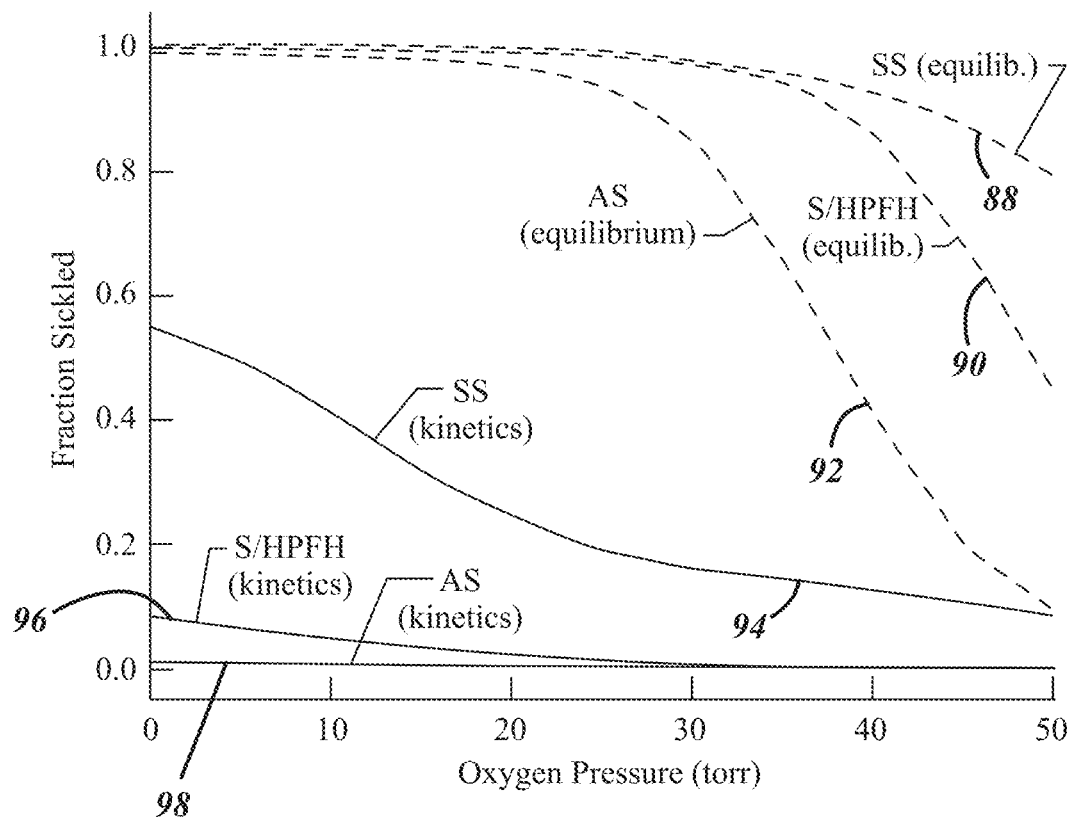
FIG. 7 is a graph, based on a graph published in Henry, E. R. et al. "Allosteric Control of Hemoglobin S Fiber Formation by Oxygen and Its Relation to the Pathophysiology of Sickle Cell Disease," 117 Proc. Natl. Acad. Sci. U.S.A. No. 126 (2020) pp 15018-027, illustrating the percentage of sickled erythrocytes as a function of changes to the partial pressure of oxygen in a supporting medium for the erythrocytes containing different types of hemoglobin when medium deoxygenation is performed at quasi-equilibrium or in a kinetic mode.

Referring to FIG. 7, the information regarding the number or percentage of sickled erythrocytes (or a particular shape or morphological form of sickled erythrocyte) obtained in step 64 may also be combined with information obtained in step 62 to generate sickling curves illustrating the amount of sickling of as a function of oxygen tension. In the illustrated embodiment, curves are shown illustrating the percentage of sickling of erythrocytes at different partial oxygen pressures in the supporting mediums for samples having different types of hemoglobin under equilibrium (curves 88, 90, 92) and under kinetic conditions (curves 94, 96, 98). In another embodiment, however, different curves may be generated for different rates of deoxygenation in supporting mediums or in Hb. Curves 88, 90, 92, 94, 96, 98 may be used to determine clinical parameters such as the point of sickling (POS) (i.e., the point on the curve when sickling or red blood cells begins), the rate of sickling, and delay in sickling. The curves 88, 90, 92, 94 96, 98 may further be used to identify multiple morphological points of sickling (as opposed to a single average point of sickling as provided in some conventional deformability-based assays), delays of sickling, the rate of sickling and cell fraction size that are attributable to different erythrocyte subpopulations such as, for example, erythrocytes that are modified by a drug or experience different levels of modification by the drug such as differences in the number of oxygen binding locations or the distribution of hemoglobin molecules modified by a drug between cells in erythrocytes in the sample (see FIG. 6, curve 78)). In yet another embodiment, the number or percentage of sickled erythrocytes over time can be compared to the rate of HB deoxygenation over time (both obtained in step 62) to assess delays in Hb polymerization.

In yet another embodiment, one of the variables obtained in step 64 may comprise heterogeneity in oxygen binding in Hb and, in particular, the amount of Hb bound to a number of oxygen molecules meeting a predetermined condition relative to a predetermined number. An Hb molecule is a tetramer containing four Hb monomers and this tetramer is capable of binding to up to four oxygen molecules. Polymerization of HbS is dependent, in part, on oxygen binding of HbS and this information may therefore be valuable in assessing various effects on erythrocytes and Hb. The number of Hb molecules or the percentage of Hb molecules bound to a given number of oxygen molecules (from zero up to four) at any given time $t_1 \ldots t_n$ may be determined using light source 34 and spectrophotometer 36 or estimated using numeric modeling methods based on medium oxygen concentration measurements by oxygen probe and the knowledge of hemoglobin oxygen dissociation curves. In some embodiments, the variable may comprise the number of Hb molecules or percentage of Hb molecules having one or two, or three, or four oxygen molecules (i.e., such that the predetermined number is one, two, three, or four and the predetermined condition is that the tetramer Hb molecule is bound to a number of oxygen molecules equaling the predetermined number). In some embodiments, the variable may comprise the number of Hb molecules or percentage of Hb molecules having less oxygen molecules or more oxygen molecules than a certain number (e.g., where the predetermined number is zero or four and the predetermined condition is that the Hb molecule is bound to a number of oxygen molecules that is greater than or less than, respectively, the predetermined number). In yet another embodiment, the variable may comprise the number of Hb molecules or percentage of Hb molecules having a number of oxygen molecules falling within a predefined range (e.g., where the predetermined number is one or two and the predetermined condition is that the Hb molecule is bound to a number of oxygen molecules equal to one or two oxygen molecules).

Referring again to FIG. 3, the method may continue with the step 100 of correlating, for the aliquot of sample A and, in certain embodiments the aliquot of sample B, values for different variables associated with the sample(s) to generate a multi-dimensional surface (i.e., a continuous boundary dividing a three-dimensional spaced into two regions). These variables may comprise variables associated with the process of deoxygenating the supporting medium in step 60 such as the predetermined level of hypoxia or predetermined rate of oxygen consumption, variables associated with the supporting medium obtained in step 62 such as the level of hypoxia or rate of deoxygenation in the supporting medium (s), variables associated with the cellular unit obtained in step 64 such as such as rate of deoxygenation of Hb or change in morphology of the cellular unit, or heterogeneity in oxygen binding in Hb and time. In one embodiment, values for one of the predetermined amount of hypoxia and the predetermined rate of oxygen consumption induced in the supporting medium in step 60 are correlated with at least two of (i) values for the other one of the predetermined amount of hypoxia and the predetermined rate of oxygen consumption induced in the supporting medium in step 60, (ii) values for one or more variables associated with the supporting medium(s) obtained in step 62 such as the level of hypoxia or rate of deoxygenation in the supporting medium(s), (iii) values for one or more variables associated with the cellular unit(s) obtained in step 64 such as rate of deoxygenation of Hb or change in morphology of the cellular unit, or heterogeneity in oxygen binding in Hb, and (iv) the plurality of different times to generate the multi-dimensional surface(s). In another embodiment, values for two different variables associated with the cellular unit(s) (e.g., the rate of deoxygenation of Hb and the change in morphology of the cellular unit(s)) may be correlated with either values for a variable associated with the supporting medium(s) (e.g., the level or rate of deoxygenation in the supporting medium(s)) or the plurality of different times to generate the multi-dimensional surface(s). Regardless of the particular combination of chosen, the values may be correlated based on the corresponding times $t_1 \ldots t_n$ those values occurred and controller 40 can therefore generate a multi-dimensional surface associated with the aliquot of the sample. As discussed below, the surfaces enable comparisons that allow enhanced assessment of effects on cellular units. The surfaces are also advantageous, however, in that they provide a better illustration of effects than conventional systems and methods are able to provide.

Referring again to FIG. 3, method may continue with the step 102 of identifying differences between the multi-dimensional surface associated with the aliquot for sample A that is subject to the effect with one or more multi-dimensional surfaces associated with other samples. In one embodiment of the invention an effect on a cellular unit is assessed by identifying differences between a surface associated with an aliquot for a sample (sample A) that is subject to the effect and a surface associated with an aliquot for a sample (sample B) including a cellular unit from the same organism that is not subject to the effect. In other embodiments, an effect on a cellular unit is assessed by identifying differences between a surface associated with an aliquot for a sample (Sample A) that is subject to the effect and a surface for a sample for another cellular unit (e.g., from a different organism or patient). In other embodiments an effect on a cellular unit is assessed by identifying differences between a surface associated with an aliquot for a sample (Sample A) that is subject to the effect and a surface that is a composite (e.g., an average) of multiple surfaces for different samples for other cellular units (e.g., from a group of different organisms or patients or a composite of cellular units obtained at different times). In yet other embodiments, an effect on a cellular unit is assessed by identifying differences between a surface associated with an aliquot for a sample (Sample A) that is subject to the effect and a surface that is formed not from the measurement of values from one or more samples, but is instead formed from artificial values configured to establish a surface meeting a predefined objective.

Step 102 may include several substeps in certain embodiments. In one embodiment step 102 may include the substeps of generating two-dimensional (2D) slices from the surfaces, identifying corresponding slices from each surface, and locating differences between the surfaces shown in the corresponding slices. The identification may be done by visual observation in some embodiments or automatically by controller 40 in other embodiments.

The identified differences may take on a variety of form. The differences may, for example, be the difference in amplitude at corresponding points on the surfaces or over the entirety of the surfaces. Alternatively, the differences may be related to the shape of the surface including the relative locations of local maximums and minimums and the amplitudes of those local maximums and minimums or the number/frequency of local maximums and/or minimums. Relevant to SCD, these differences may comprise differences in the number of sickled erythrocytes or reversibly sickled erythrocytes and/or the particular morphological forms of each. Notably, the multi-dimensional surfaces not only improve the ability to illustrate the impact of various effects on cellular units, but also facilitate identification of conditions where any differences are at their greatest extent or least amplified so that future assessments can be targeted to replicate those conditions.

Figure 8:
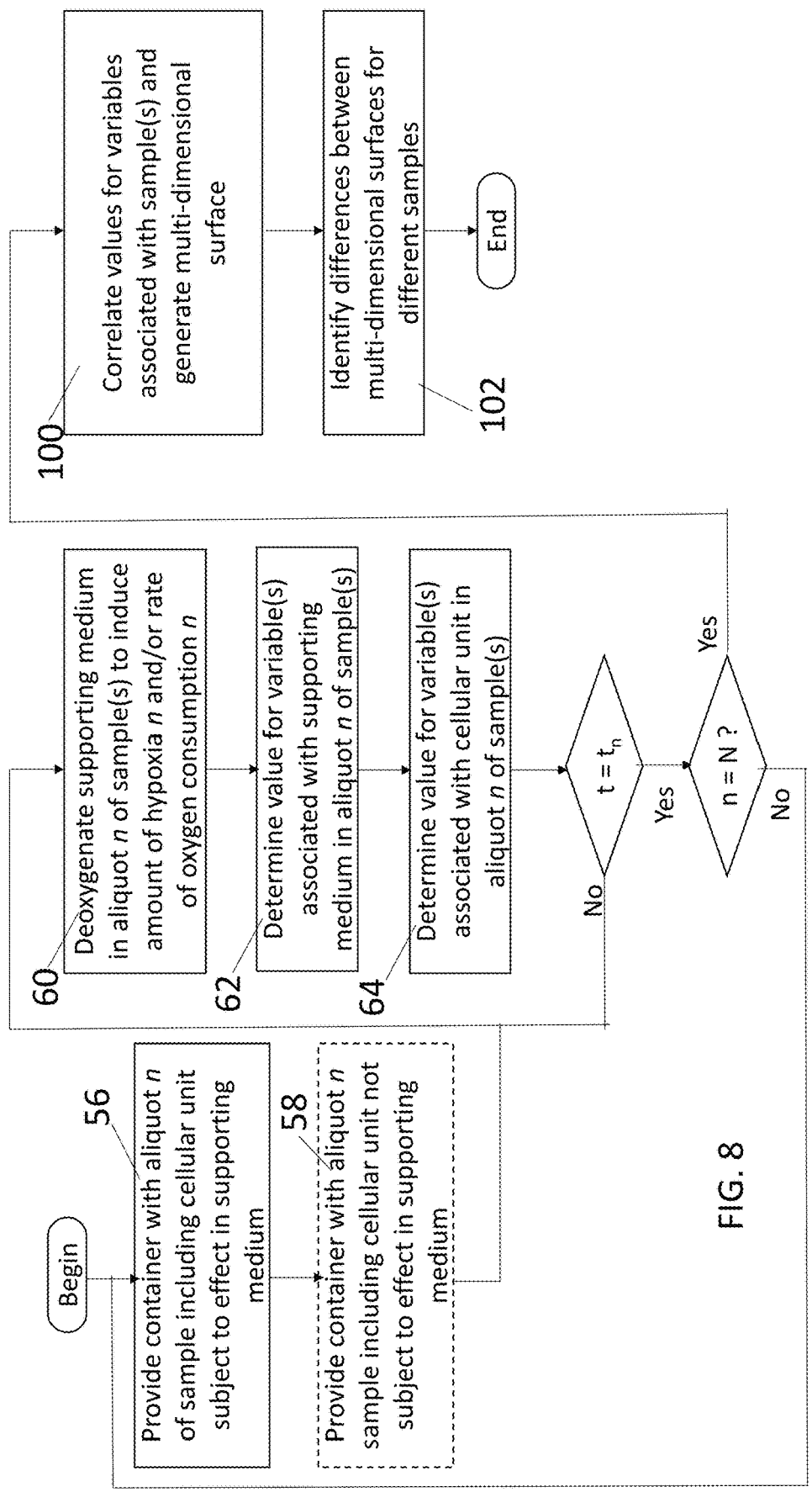
FIG. 8 is a flowchart illustrated a method in accordance with other embodiments of the invention.
Figure 9C:
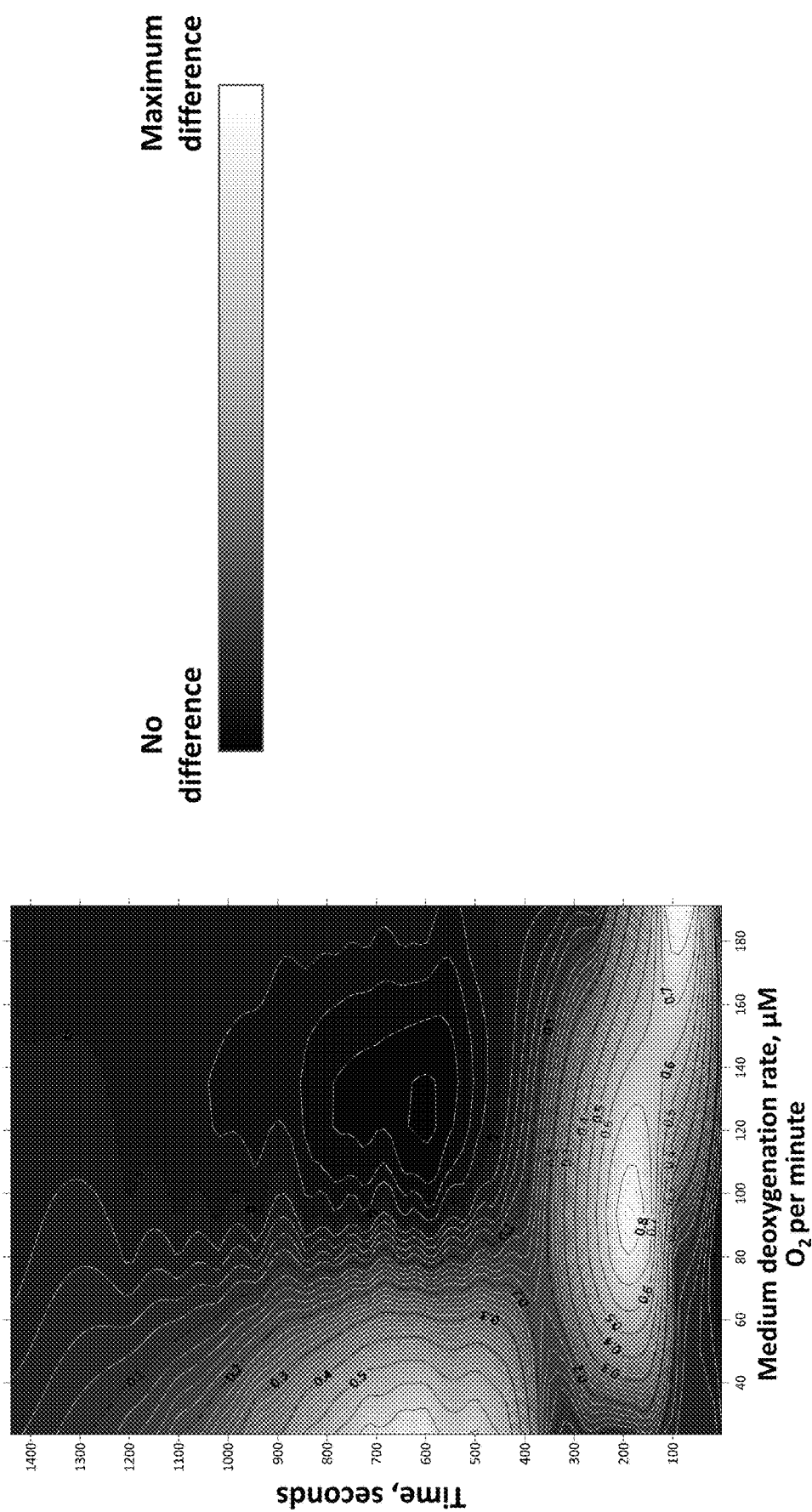
FIG. 9C is a contour maps illustrating the differences between FIGS. 9A-9B.

The embodiments of the method described above involve deoxygenating a single aliquot of a sample A including a cellular unit subject to an effect by inducing at least one of a predetermined amount of hypoxia and a predetermined rate of oxygen consumption in the supporting medium and then eventually comparing a multi-dimensional surface derived from values obtained during the deoxygenation against a surface associated with one or more aliquots of one or more other sample(s) (e.g., a sample B including a cellular unit not subject to the effect). Referring now to FIG. 8, in accordance with other embodiments, multiple aliquots of a sample may be deoxygenated to induce different predetermined amounts of hypoxia and/or different predetermined rates of oxygen consumption in the supporting mediums for each aliquot of the sample. In one embodiment, for example, multiple aliquots of a sample A including a cellular unit subject to effect and multiple aliquots of a sample B including a cellular unit not subject to the effect may be deoxygenated to induce different predetermined amounts of hypoxia and/or different predetermined rates of oxygen consumption in the supporting mediums for each aliquot in order to generate additional information regarding the impact of hypoxia on cellular units in the samples. Steps 56, 58, 60, 62, and 64 would progress in substantially the same manner discussed hereinabove with the exception that the steps would be repeated on different aliquots n where n=1 . . . N of a sample and deoxygenation of the supporting medium in each aliquot of a sample in step 60 would induce at least one of a different amount of hypoxia and a different rate of oxygen consumption in the supporting medium.

Once steps 56, 58, 60, 62, and 64 are performed on a final aliquot N of the sample(s), the method may again proceed with the step 100 of correlating, for the aliquots of sample A and, in certain embodiments the aliquots of sample B, values for different variables associated with the sample(s) to generate a multi-dimensional surface(s). Unlike the prior embodiments described above, however, one dimension in the surface will comprise the varying values for the amount of hypoxia or rate of oxygen consumption applied to the supporting mediums for the different aliquots of the samples. In one embodiment, controller 40 will correlate at least one of the predetermined amount of hypoxia and the predetermined rate of oxygen consumption for each aliquot of a sample with corresponding values for a variable associated with the cellular unit in the aliquot of the sample and time to generate a first multi-dimensional surface for each sample.

Figure 10B:
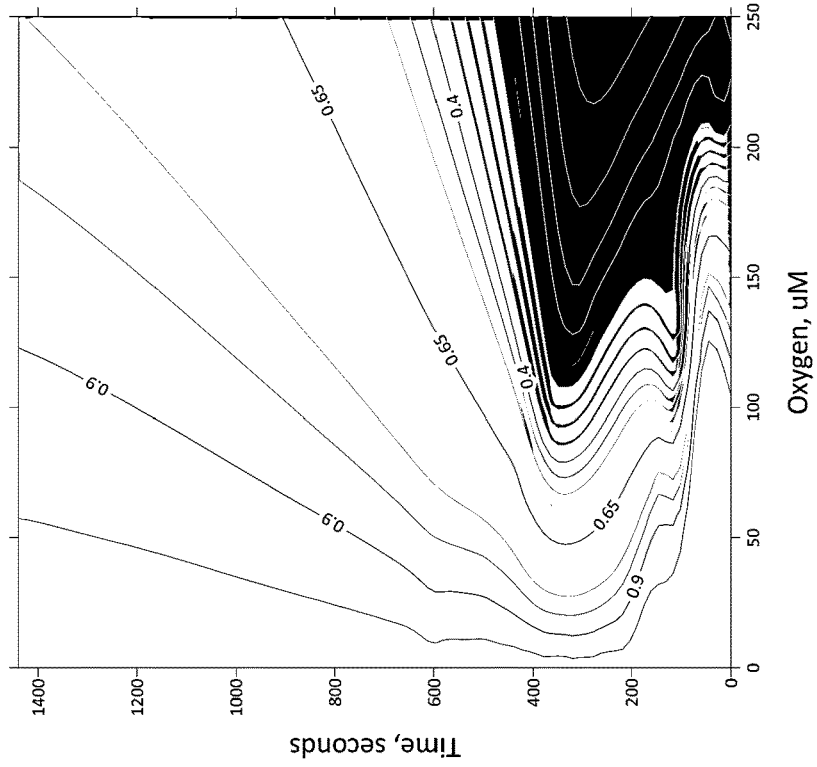
FIGS. 10A-10B are contour maps illustrating sections of multi-dimensional surfaces correlating values for time, the level of deoxygenation of a supporting medium, and erythrocyte sickling for multiple aliquots of sample subject to an effect (FIG. 10A) and a sample not subject to an effect (FIG. 10B) obtained from deoxygenation of the aliquots to different predetermined amounts of hypoxia, but at the same predetermined rates of hypoxia.
Figure 10A:
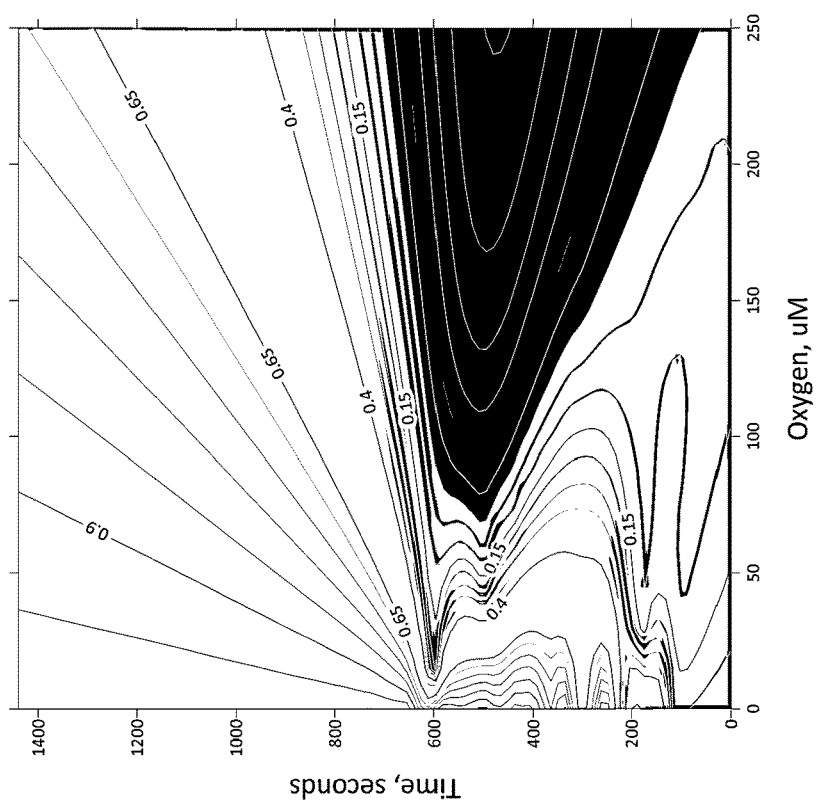

Referring now to FIGS. 9A-9B and 10A-10B, representative sections of multi-dimensional surfaces generated using the method of FIG. 8 are illustrated. FIGS. 9A-9B and 10A-10B illustrate contour maps comprising three-dimensional cross-sections of four-dimensional surfaces generated using the method of FIG. 8. The contour maps in FIGS. 9A-9B relate values for time, a variable associated with the supporting medium in the form of the rate of deoxygenation in the supporting medium, and a variable associated with the cellular unit in the form of an amount of erythrocyte sickling for aliquots of a sample A (FIG. 9A) subject to an effect (a drug in the illustrated embodiment) and a sample B (FIG. 9B) not subject to the effect that were obtained from deoxygenation of the aliquots to the same predetermined amount of hypoxia, but at different predetermined rates of oxygen consumption. FIGS. 10A-10B relate values for time, a variable associated with the supporting medium in the form of the level of hypoxia in the supporting medium, and variable associated with the cellular unit in the form of the amount of erythrocyte sickling for aliquots of a sample A (FIG. 10A) subject to an effect (a drug in the illustrated embodiment) and a sample B (FIG. 10B) not subject to the effect that were obtained from deoxygenation of the aliquots to different predetermined amounts of hypoxia, but at the same predetermined rate of oxygen consumption.

Referring again to FIG. 8, the method may again conclude with step 102 of identifying differences between the multi-dimensional surface associated with the aliquots for sample A that is subject to the effect with one or more multi-dimensional surfaces associated with other samples. In one embodiment of the invention an effect on a cellular unit is assessed by identifying differences between a surface associated with aliquots of a sample (sample A) that is subject to the effect and a surface associated with aliquots of a sample (sample B) including a cellular unit from the same organism that is not subject to the effect. In other embodiments, an effect on a cellular unit is assessed by identifying differences between a surface associated with aliquots of a sample (Sample A) that is subject to the effect and a surface for aliquots of a sample for another cellular unit (e.g., from a different organism or patient). In other embodiments an effect on a cellular unit is assessed by identifying differences between a surface associated with aliquots of a sample (Sample A) that is subject to the effect and a surface that is a composite (e.g., an average) of multiple surfaces for aliquots of different samples for other cellular units (e.g., from a group of different organisms or patients or a composite of cellular units obtained at different times). In yet other embodiments, an effect on a cellular unit is assessed by identifying differences between a surface associated with an aliquot of a sample (Sample A) that is subject to the effect and a surface that is formed not from the measurement of values from one or more samples, but is instead formed from artificial values configured to establish a surface meeting a predefined objective.

Step 102 may again include several substeps in certain embodiments. In one embodiment step 102 may include the substeps of generating slices from the surfaces, identifying corresponding slices from each surface, and locating differences between the surfaces shown in the corresponding slices. The identification may again be done by visual observation in some embodiments or automatically by controller 40 in other embodiments. The identified differences may again take on a variety of form. The differences may, for example, be the difference in amplitude at corresponding points on the surfaces or over the entirety of the surfaces. Alternatively, the differences may be related to the shape of the surface including the relative locations of local maximums and minimums and the amplitudes of those local maximums and minimums or the number/frequency of local maximums and/or minimums. Relevant to SCD, these differences may comprise differences in the number of sickled erythrocytes or the particular morphological forms reached as a result of medium deoxygenation.

A system and method for assessing an effect on a cellular unit of an organism in accordance the present teachings represent an improvement as compared to conventional systems and methods. The system and method enable assessment of an effect at varying levels and rates of hypoxia and also under both equilibrium and non-equilibrium conditions to more accurately reflect in vivo conditions.

While the invention has been shown and described with reference to one or more particular embodiments thereof, it will be understood by those of skill in the art that various changes and modifications can be made without departing from the spirit and scope of the invention. For example, the over molding and clamping technology disclosed herein is not limited to wheel speed sensors, but may also be used for other sensors having similar mounting arrangements including transmission sensors and crankshaft sensors.

What is claimed is:

1. A method for assessing an effect on a cellular unit of an organism, comprising the steps of:
    providing a first aliquot of a first sample including a first cellular unit not subject to the effect in a first supporting medium in a first hermetically sealed container;
    providing a first aliquot of a second sample including a second cellular unit subject to the effect in a second supporting medium in a second hermetically sealed container;
    deoxygenating the first supporting medium and the second supporting medium to induce at least one of a predetermined amount of hypoxia and a predetermined rate of oxygen consumption in the first supporting medium and in the second supporting medium;
    determining, during deoxygenation of the first supporting medium, values for one or more variables associated with the first supporting medium at each of a first plurality of different times and/or values for one or more variables associated with the first cellular unit at each of the first plurality of different times;
    determining, during deoxygenation of the second supporting medium, values for one or more variables associated with the second supporting medium at each of a second plurality of different times and/or values for one or more variables associated with the second cellular unit at each of the second plurality of different times;
    correlating one of the predetermined amount of hypoxia and the predetermined rate of oxygen consumption in the first supporting medium with at least two of the other one of the predetermined amount of hypoxia and the predetermined rate of oxygen consumption in the first supporting medium, the values for the one or more variables associated with the first supporting medium, the values for the one or more variables associated with the first cellular unit and the first plurality of different times to generate a first multi-dimensional surface;
    correlating one of the predetermined amount of hypoxia and the predetermined rate of oxygen consumption in the second supporting medium with at least two of the other one of the predetermined amount of hypoxia and the predetermined rate of oxygen consumption in the second supporting medium, the values for the one or more variables associated with the second supporting medium, the values for the one or more variables associated with the second cellular unit and the second plurality of different times to generate a second multi-dimensional surface;
    identifying differences between the first multi-dimensional surface and the second multi-dimensional surface.

2. The method of claim 1 wherein the effect comprises a treatment.

3. The method of claim 2 wherein the treatment comprises a medication.

4. The method of claim 1 wherein the effect comprises a disease.

5. The method of claim 4 wherein the disease comprises sickle cell disease.

6. The method of claim 1 wherein the effect comprises a passage of time.

7. The method of claim 1 wherein the step of deoxygenating the first and second supporting mediums includes the substep of introducing a first amount of a reaction substrate and a second amount of a reaction enzyme into both of the first and second hermetically sealed containers, the first amount of the reaction substrate and the second amount of the reaction enzyme selected to induce at least one of the predetermined amount of hypoxia and the predetermined rate of oxygen consumption in the first and second supporting mediums during a reaction between the reaction substrate and the reaction enzyme.

8. The method of claim 7 wherein the reaction substrate comprises protocatechuic acid and the reaction enzyme comprises protocatechuate dioxygenase.

9. The method of claim 1 wherein the one or more variables associated with the first supporting medium comprises a level of hypoxia in the first supporting medium and the one or more variables associated with the second supporting medium comprises a level of hypoxia in the second supporting medium.

10. The method of claim 1 wherein the one or more variables associated with the first supporting medium comprises a rate of deoxygenation in the first supporting medium and one or more variables associated with the second supporting medium comprises a rate of deoxygenation in the second supporting medium.

11. The method of claim 1 wherein the first cellular unit comprises hemoglobin and the one or more variables associated with the first cellular unit comprises a rate of hemoglobin deoxygenation in the first cellular unit and the second cellular unit comprises hemoglobin and the one or more variables associated with the second cellular unit comprises a rate of hemoglobin deoxygenation in the second cellular unit.

12. The method of claim 1 wherein the first cellular unit comprises hemoglobin and the one or more variables associated with the first cellular unit comprises a level of deoxygenation of hemoglobin in the first cellular unit and the second cellular unit comprises hemoglobin and the one or more variables associated with the second cellular unit comprises a level of deoxygenation of hemoglobin in the second cellular unit.

13. The method of claim 1 wherein the first cellular unit comprises an erythrocyte and the one or more variables associated with the first cellular unit comprises a change in morphology of the first cellular unit and the second cellular unit comprises an erythrocyte and the one or more variables associated with the second cellular unit comprises a change in morphology of the second cellular unit.

14. The method of claim 1 wherein the first cellular unit comprises hemoglobin and the one or more variables associated with the first cellular unit comprises a heterogeneity in oxygen binding in the first cellular unit and the second cellular unit comprises hemoglobin and the one or more variables associated with the second cellular unit comprises a heterogeneity in oxygen binding in the second cellular unit.

15. The method of claim 1 wherein the predetermined rate of oxygen consumption results in a rate of change in the one or more variables associated with the first cellular unit that is smaller than a rate of deoxygenation in the first supporting medium and a rate of change in the one or more variables associated with the second cellular unit that is smaller than a rate of deoxygenation in the second supporting medium.

16. The method of claim 1 wherein each of the first and second hermetically sealed containers have an interior surface coated with a protein configured to interact with corresponding ones of the first and second cellular units.

17. A method for assessing an effect on a cellular unit of an organism, comprising the steps of:
providing a first aliquot of a first sample including a first cellular unit not subject to the effect in a first supporting medium in a first hermetically sea led container;
providing a first aliquot of a second sample including a second cellular unit subject to the effect in a second supporting medium in a second hermetically sealed container;
deoxygenating the first supporting medium and the second supporting medium to induce at least one of a predetermined amount of hypoxia and a predetermined rate of oxygen consumption in the first supporting medium and in the second supporting medium;
determining, during deoxygenation of the first supporting medium, values for one or more variables associated with the first supporting medium at each of a first plurality of different times and/or values for two or more variables associated with the first cellular unit at each of the first plurality of different times;
determining, during deoxygenation of the second supporting medium, values for one or more variables associated with the second supporting medium at each of a second plurality of different times and/or values for two or more variables associated with the second cellular unit at each of the second plurality of different times;
correlating values for a first variable associated with the first cellular unit, values for a second variable associated with the first cellular unit and at least one of the values for a first variable associated with the first supporting medium and the first plurality of times to generate a first multi-dimensional surface;
correlating values for a first variable associated with the second cellular unit, values for a second variable associated with the second cellular unit and at least one of values for a first variable associated with the second supporting medium and the second plurality of times to generate a second multi-dimensional surface;
identifying differences between the first multi-dimensional surface and the second multi-dimensional surface.

18. The method of claim 17 wherein the predetermined rate of oxygen consumption results in a rate of change in at least one of the two or more variables associated with the first cellular unit that is smaller than a rate of deoxygenation in the first supporting medium and a rate of change in at least one of the two or more variables associated with the second cellular unit that is smaller than a rate of deoxygenation in the second supporting medium.

19. A method for assessing an effect on a cellular unit of an organism, comprising the steps of:
providing a first aliquot of a first sample including a first cellular unit not subject to the effect in a first supporting medium in a first hermetically sealed container;
providing a first aliquot of a second sample including a second cellular unit subject to the effect in a second supporting medium in a second hermetically sealed container;
deoxygenating the first supporting medium and the second supporting medium to induce at least one of a first predetermined amount of hypoxia and a first predetermined rate of oxygen consumption in the first supporting medium and in the second supporting medium;
determining, during deoxygenation of the first supporting medium, a value for at least one variable associated with the first cellular unit at each of a first plurality of different times;
determining, during deoxygenation of the second supporting medium, a value for at least one variable associated with the second cellular unit at each of a second plurality of different times;
providing a second aliquot of the first sample including a third cellular unit not subject to the effect in a third supporting medium in a third hermetically sealed container;
providing a second aliquot of the second sample including a fourth cellular unit subject to the effect in a fourth supporting medium in a fourth hermetically sealed container;
deoxygenating the third supporting medium and the fourth supporting medium to induce at least one of a second predetermined amount of hypoxia and a second predetermined rate of oxygen consumption in the third supporting medium and in the fourth supporting medium;
determining, during deoxygenation of the third supporting medium, a value for at least one variable associated with the third cellular unit at each of a third plurality of different times;
determining, during deoxygenation of the fourth supporting medium, a value for at least one variable associated with the fourth cellular unit at each of a fourth plurality of different times;
correlating the at least one of the first predetermined amount of hypoxia and the first predetermined rate of oxygen consumption with the values for the at least one variable associated with the first cellular unit and the first plurality of different times and correlating the at least one of the second predetermined amount of hypoxia and the second predetermined rate of oxygen consumption with the values for the at least one variable associated with the third cellular unit and the third plurality of different times to generate a first multi-dimensional surface;

correlating the at least one of the first predetermined amount of hypoxia and the first predetermined rate of oxygen consumption with the values for the at least one variable associated with the second cellular unit and the second plurality of different times and correlating the at least one of the second predetermined amount of hypoxia and the second predetermined rate of oxygen consumption with the values for the at least one variable associated with the fourth cellular unit and the fourth plurality of different times to generate a second multi-dimensional surface;

identifying differences between the first multi-dimensional surface and the second multi-dimensional surface.

20. The method of claim 19 wherein the first predetermined rate of oxygen consumption results in a rate of change in at the at least one variable associated with the first cellular unit that is smaller than a rate of deoxygenation in the first supporting medium and a rate of change in the at least one variable associated with the second cellular unit that is smaller than a rate of deoxygenation in the second supporting medium and the second predetermined rate of oxygen consumption results in a rate of change in at the at least one variable associated with the third cellular unit that is smaller than a rate of deoxygenation in the third supporting medium and a rate of change in the at least one variable associated with the fourth cellular unit that is smaller than a rate of deoxygenation in the fourth supporting medium.

* * * * *